United States Patent
Ling et al.

(10) Patent No.: US 11,361,569 B2
(45) Date of Patent: Jun. 14, 2022

(54) HIERARCHICAL NEURAL NETWORKS WITH GRANULARIZED ATTENTION

(71) Applicant: KONINKLIJKE PHILIPS N.V., Eindhoven (NL)

(72) Inventors: Yuan Ling, Somerville, MA (US); Sheikh Sadid Al Hasan, Cambridge, MA (US); Oladimeji Feyisetan Farri, Yorktown Heights, NY (US); Junyi Liu, Windham, NH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 97 days.

(21) Appl. No.: 16/634,624

(22) PCT Filed: Aug. 3, 2018

(86) PCT No.: PCT/EP2018/071158
§ 371 (c)(1),
(2) Date: Jan. 28, 2020

(87) PCT Pub. No.: WO2019/025601
PCT Pub. Date: Feb. 7, 2019

(65) Prior Publication Data
US 2021/0089765 A1  Mar. 25, 2021

Related U.S. Application Data

(60) Provisional application No. 62/540,790, filed on Aug. 3, 2017, provisional application No. 62/699,079, filed on Jul. 17, 2018.

(51) Int. Cl.
*G06K 9/00* (2022.01)
*G06V 30/414* (2022.01)
(Continued)

(52) U.S. Cl.
CPC .......... *G06V 30/414* (2022.01); *G06K 9/6257* (2013.01); *G06N 3/04* (2013.01); *G16H 50/20* (2018.01)

(58) Field of Classification Search
CPC .. G06K 9/00463; G06K 9/6257; G16H 50/20; G06N 3/04; G06F 16/35
(Continued)

(56) References Cited

U.S. PATENT DOCUMENTS 5,930,788 A * 7/1999 Wical .................... G06F 16/353
6,606,620 B1 * 8/2003 Sundaresan ............ G06F 16/30
(Continued)

FOREIGN PATENT DOCUMENTS

EP    2996053    3/2016

OTHER PUBLICATIONS

Yang, "Hierarchical Attention Networks for Document Classification," Proceedings of the 2016 Conference of the North American Chapter of the Association for Computational Linguistics: Human Language Technologies. Jun. 12, 2016 pp. 1480-1489. (Year: 2016).*
(Continued)

*Primary Examiner* — Juan A Torres

(57) ABSTRACT

Techniques are provided for generating and applying a granular attention hierarchical neural network model to classify a document. In various embodiments, data indicative of the document may be obtained (102) and processed (104) into a first layer of two or more layers of a hierarchical network model using a dual granularity attention mechanism to generate first layer output data, wherein the dual granularity attention mechanism weighs some portions of the data indicative of the document more heavily. Some portions of the data indicative of the document are integrated into the hieratical network model during training of the dual granularity attention mechanism. The first layer output data may
(Continued)

be processed (106) in the second of two or more layers of the hierarchical network model to generate second layer output data. A classification label can be generated (108) from the second layer output data.

18 Claims, 20 Drawing Sheets

(51) Int. Cl.
  *G16H 50/20* (2018.01)
  *G06K 9/62* (2022.01)
  *G06N 3/04* (2006.01)
(58) Field of Classification Search
  USPC .......................................................... 382/190
  See application file for complete search history.

(56) References Cited

U.S. PATENT DOCUMENTS

| | | | |
|---|---|---|---|
| 8,484,245 B2 * | 7/2013 | Ha-Thuc | G06F 16/35 707/777 |
| 8,725,732 B1 * | 5/2014 | Jeh | G06F 16/353 707/736 |
| 10,657,186 B2 * | 5/2020 | Gates | G06F 16/93 |
| 2002/0138529 A1 * | 9/2002 | Yang-Stephens | G06F 16/35 715/256 |
| 2011/0137898 A1 | 6/2011 | Gordo | |
| 2012/0065987 A1 | 3/2012 | Farooq | |
| 2015/0310000 A1 * | 10/2015 | Schijvenaars | G06F 16/382 707/738 |
| 2016/0078022 A1 * | 3/2016 | Lisuk | G06F 40/117 706/12 |

OTHER PUBLICATIONS

International Search Report and Written Opinion dated Nov. 22, 2018 for International Application No. PCT/EP2018/071158 Filed Aug. 3, 2018.

Chen, et al: "Neural Sentiment Classification with User and Product Attention", Proceedings of the 2016 Conference on Empirical Methods in Natural Language Processing, pp. 1650-1659, Austin, Texas, Nov. 1-5, 2016.

Chapman, et al: "Document-Level Classification of CT Pulmonary Angiography Reports based on an Extension of the ConText Algorithm", J Biomed Inform. Oct. 2011 ; 44(5): 728-737.

Yang, et al: "Hierarchical Attention Networks for Document Classification", Association for Computational Linguistics, 2016.

\* cited by examiner

150

```
┌─────────────────────────────────────────────────────────────┐
│ Processing data indicative of a character representation of │
│ a document in a character layer of a hierarchical network   │
│ model using a character multiple granularity attention      │
│ mechanism to generate data inticative of a word             │
│ representation, where the dual granularity attention        │
│ mechanism weighs some portions of the data more heavily     │
│                           152                               │
└─────────────────────────────────────────────────────────────┘
                              │
                              ▼
┌─────────────────────────────────────────────────────────────┐
│ Processing the data indicative of a word representation in  │
│ a word layer of the hierarichal network model using a word  │
│ multiple granularity attention mechanism to generate data   │
│ indicative of a sentence representation                     │
│                           154                               │
└─────────────────────────────────────────────────────────────┘
                              │
                              ▼
┌─────────────────────────────────────────────────────────────┐
│ Processing the data indicatative of a sentence              │
│ representation in a sentence layer of the hierarichical     │
│ network model using a sentence multiple granularity         │
│ attention mechanism to generate data indicative of a        │
│ section representation                                      │
│                           156                               │
└─────────────────────────────────────────────────────────────┘
                              │
                              ▼
┌─────────────────────────────────────────────────────────────┐
│ Processing the data indicatative of a section               │
│ representation in a section layer of the hierarchical       │
│ network model using a section multiple granularity          │
│ attention mechanism to generate data indicative of the      │
│ document                                                    │
│                           158                               │
└─────────────────────────────────────────────────────────────┘
                              │
                              ▼
┌─────────────────────────────────────────────────────────────┐
│ Processing a document classification label from the data    │
│ indicative of the document                                  │
│                           160                               │
└─────────────────────────────────────────────────────────────┘
                              │
                              ▼
┌─────────────────────────────────────────────────────────────┐
│ Providing the document classification label using a         │
│ computing system to a user                                  │
│                           162                               │
└─────────────────────────────────────────────────────────────┘
```

FIG. 1B

```
                                          ┌─ 802
Pulmonary Emboli (PE) predict: positive
Sentence 1: impression 1 interval decrease in the volume of clot
            within the pulmonary arterial system Sentence 2: 2 decreased patchy consolidation and ground glass
            opacity in both lungs, as described above Sentence 3: these may represent areas of resolving hemorrhage or infection
```

FIG. 8A

```
                                          ┌─ 850
Pulmonary Emboli (PE) predict: negative
Sentence 1: 1 generalized enlargement of the aortic root 2 d orthogonal
            measurements are provided above and subsequent
            3 d measurements will be provided by the 3 d laboratory the aorta
            is dilated from the level of the aortic annulus up to the mid arch Sentence 2: 2 coronary artery disease and atherosclerosis Sentence 3: there is no filling defect in the central pulmonary artery to
            indicate a pulmonary embolism Sentence 4: 3 left ventricular enlargement likely indicates cardiomyopathy Sentence 5: 4 biventricular pacer and defibrillator leads in the expected position
```

FIG. 8B

Sample report

Sentence 1: impression 1 at least 2 pulmonary nodules that are most suggestive of pulmonary metastases Sentence 2: 2 multifocal peripheral airspace consolidated in both lungs Sentence 3: differential diagnosis includes pulmonary infarcts from pulmonary emboli, septic emboli, or multifocal pneumonia Sentence 4: although study was not optimized for the detection of pulmonary emboli, there is a filling defect associated with an area of airspace disease in the left upper lobe Sentence 5: a ct pe is recommended for further evaluation Sentence 6: 3 dilated, fluid filled esophagus, with debris in the left lower lobe subsegmental airways, consitent with aspiration Sentence 7: 4 expensive peritoneal carcinomatosis, with associated ascites, and new mild bilateral hyroureteronephrosis Sentence 8: 5 new, mild intrahepatic biliary ductal dilation, without an identified obstruction lesion Sentence 9: the common bile duct is normal caliber

FIG. 9A

DP examples:
pulmonary embolism or deep venous thrombosis
superior segment of the left lower lobe
right lower lobe
deep venous thrombosis
ct chest abdomen and pelvis with contrast
superior segment of the right lower lobe
.....

1200

```
Pulmonary Emboli (PE) predict: positive
Sentence 1: impression 1 interval decrease in the volume of clot
            within the pulmonary arterial system Sentence 2: 2 decreased patchy consolidation and ground glass
            opacity in both lungs, as described above Sentence 3: these may represent areas of resolving hemorrhage or infection
```

```
Pulmonary Emboli (PE) predict: negative
Sentence 1: generalized enlargement of the aortic root 2 d orthogonal
            measurements are provided above and subsequent
            3 d measurements will be provided by the 3 d laboratory the aorta
            is dilated from the level of the aortic annulus up to the mid arch Sentence 2: 2 coronary artery disease and atherosclerosis Sentence 3: there is no filling defect in the central pulmonary artery to indicate
            a pulmonary embolism Sentence 4: 3 left ventricular enlargement likely indicates cardiomyopathy Sentence 5: 4 biventricular pacer and defibrillator leads in the expected
            position
```

Pulmonary Emboli (PE) predict: negative

Sentence 1: impression 1 at least 2 pulmonary nodules that are most suggestive of pulmonary metastases Sentence 2: 2 multifocal peripheral airspace consolidation in both lungs Sentence 3: differential diagnosis includes pulmonary infarcts from pulmonary emboli, septic emboli, or multifocal pneumonia Sentence 4: although the study was not optimized for the detection of pulmonary emboli, there is a filling defect associated with an area of airspace disease in the left upper lobe Sentence 5: a ct pe is recommended for further evaluation Sentence 6: 3 dilated, fluid filled esophagus, with debris in the left lower lobe subsegmental airways, consistent with aspiration Sentence 7: 4 extensive peritoneal carcinomatosis, with associated ascites, and new mild bilateral hydroureteronephrosis Sentence 8: 5 new, mild intrahepatic biliary ductal dilation, without an identified obstructing lesion Sentence 9: the common bile duct is normal caliber Sentence 10: 6 anasarca Sentence 11: i have personally reviewed the images for this examination and agreed with the report transcribed above

Pulmonary Emboli (PE) predict: positive

Sentence 1: 1 due mainly to increased noise secondary to patient's body habitus, there is still insufficient image quality to completely rule out pulmonary embolus Sentence 2: in the scan, no definite pulmonary embolus is seen in the lobar and segmental arteries Sentence 3: there is streak artifact versus possible pulmonary embolus in the right upper lobe segmental pulmonary artery Sentence 4: if there is continued clinical concern for pulmonary embolus a vq scan may be the only way to rule out pulmonary embolus Sentence 5: 2 redemonstration of anterior mediastinal soft tissue mass, that has been incompletely evaluated on this ct scan Sentence 6: recommend further evaluation with mri or biopsy

Sentence 1: impression 1 at least 2 pulmonary nodules that are most suggestive of pulmonary metastases Sentence 2: 2 multifocal peripheral airspace consolidation in both lungs Sentence 3: differential diagnosis includes pulmonary infarcts from pulmonary emboli, septic emboli, or multifocal pneumonia Sentence 4: although the study was not optimized for the detection of pulmonary emboli, there is a filling defect associated with an area of airspace disease in the left upper lobe Sentence 5: a ct pe is recommended for further evaluation Sentence 6: 3 dilated, fluid filled esophagus, with debris in the left lower lobe subsegmental airways, consistent with aspiration Sentence 7: 4 extensive peritoneal carcinomatosis, with associated ascites, and new mild bilateral hydroureteronephrosis Sentence 8: 5 new, mild intrahepatic biliary ductal dilation, without an identified obstructing lesion Sentence 9: the common bile duct is normal caliber Sentence 10: 6 anasarca Sentence 11: i have personally reviewed the images for this examination and agreed with the report transcribed above

| | |
|---|---|
| Sentence 1: | 1 non opacification of the right middle lobe pulmonary artery, with lack of enhancement of the dependent consolidation in the lateral segment of the right middle lobe parenchyma suggests occlusive clot and segmental infarct within the right middle lobe |
| Sentence 2: | there is no evidence of any other filling defects within the pulmonary arterial tree, which appears sowewhat unusual, and might indicate that the middle lobe clot embolus is subacute |
| Sentence 3: | \ ( consider follow up, also to rule out mass, if clinically indicated \ ) 2 moderate sized right pleural effusion |
| Sentence 4: | 3 multiple scattered small foci of consolidation and ground glass opacities throughout the left lung, which may be inflammatory or infectious in etiology |
| Sentence 5: | 4 cardiomegaly, mild edema |
| Sentence 6: | 5 mild liver nodularity suggestive of cirrhosis |
| Sentence 7: | 6 the findings were discussed with dr jose at approximately 1000 hours on 10 16 08 |

FIG. 15B

HIERARCHICAL NEURAL NETWORKS WITH GRANULARIZED ATTENTION

CROSS REFERENCE TO RELATED APPLICATIONS

This application is the U.S. National Phase application under 35 U.S.C. § 371 of International Application No. PCT/EP2018/071158 filed Aug. 3, 2018, published as WO 2019/025601 on Feb. 7, 2019, which claims the benefit of U.S. Provisional Patent Application No. 62/540,790 filed Aug. 3, 2017 and U.S. Provisional Patent Application No. 62/699,079 filed Jul. 17, 2018. These applications are hereby incorporated by reference herein.

TECHNICAL FIELD

Various embodiments described herein are directed generally to natural language processing. More particularly, but not exclusively, various methods and apparatus disclosed herein relate to hierarchical network models with multiple granularity attention mechanisms.

BACKGROUND

In traditional machine learning methods for classification of free text documents (such as radiology reports), domain-specific feature engineering can be performed to consider task-oriented key features. Deep learning techniques including Convolutional Neural Networks ("CNNs") and/or Recurrent Neural Networks ("RNNs") have shown improved performance over traditional machine learning methods for text classification. However, deep neural network models generally learn task-specific features from plain raw textual data and do not emphasize important features based on multiple granularities of a document.

SUMMARY

The present disclosure is directed to methods and apparatus for hierarchical network models with multiple granularity attention mechanisms for document classification. In a variety of embodiments, the inherent structure found in documents in various domains can be utilized within the hierarchical network model. Characters, words, phrases, sentences, sections (i.e., a group under a single heading, a paragraph, etc.), etc. can be assigned different weights based on their relevance to accurately classifying documents. In some embodiments, performing document classification using hierarchal models having weights learned using techniques described herein can facilitate extensive weight visualization and analysis across different granularities. In various embodiments, a granularized attention-based hierarchical neural network ("HNN-GA") can be used in document classification (e.g., radiology report document classification, classification within other document domains, a search tool where a model can search a document at several levels of granularity, etc.). A HNN-GA can have a hierarchical structure that represents documents at different levels and/or granularities. Document levels can include characters, words, phrases, sentences, sections, etc. Additionally or alternatively, attention mechanisms based on words, phrases, sentences, paragraphs, etc. can emphasize the information which can play a role in accurate classification using a HNN-GA.

Inherent structures in different levels of granularities of a document such as characters, words, sentences, and sections possess important contextual features that can be considered and learned by neural network classification models to further improve on classification of semantically-rich documents (such as radiology reports). Many neural network models, including deep learning network models, can utilize an attention mechanism. Generally an attention mechanism can allow a network model to learn to focus on specific input data to the model. Generally, attention mechanisms are an interface formulated by parameters to focus on local and/or global features and can be evaluated by a computing system using one or more expressions.

Computing systems can employ techniques described herein for repetitive tasks in textual processing workflows. For example, in a radiology workflow, techniques described herein can be used to automatically generate radiology report classifications to filter necessary information in a textual radiology report that should be brought to the attention of the radiologists. This can enable radiologists to devote more efforts and cognitive capabilities to more difficult diagnostic reasoning tasks. Existing natural language processing ("NLP") systems can use lexical cues and context from radiology reports classification. These existing NLP systems can provide suboptimal accuracy and can have difficulties adapting to new datasets. In addition, inherent document structures based on multiple granularities are not utilized in existing frameworks.

In many embodiments, a HNN-GA can include a RNN. Additionally or alternatively, a HNN-GA can include one or more long short-term memory ("LSTM") networks (or gated recurrent units, or "GRUs," in some cases) which can be utilized for textual document classification. In a variety of embodiments, a document can be provided as a set of characters to an HNN-GA. The HNN-GA can encode the characters via hidden units in an LSTM network. The output of the LSTM network at a character layer can in turn be used in the HNN-GA to subsequently encode words, sentences, sections, and document representations in a similar fashion. Tokenized words, phrases, sentences, sections, etc. can be attached via an attention layer. For example, a word attention layer can be included in the word layer of the HNN-GA to learn weights to understand which words are more important for the underlying task domain.

In some embodiments, an attention mechanism can include dual granularity. In other words, an attention mechanism can comprise an attention history that learns what data to focus on from received input as well as a dual layer (i.e., second layer) of attention history which can include domain knowledge. In some such embodiments, the dual layer of attention history can include domain knowledge relevant to a different layer. For example, in a dual granularity attention history for a word layer, a word attention can learn weights to understand important words for the underlying domain. For example, in a dual layer attention history a first attention mechanism can include word knowledge and a second attention mechanism can be prepopulated with domain knowledge relevant to subsequent layers. For example, a second attention mechanism in a dual granularity attention mechanism for a word layer can be prepopulated with phrase domain knowledge. A domain attention history can be prepopulated with domain relevant information. For example, the top N phrases (e.g., which can be based on term frequency) from a set of documents related to a specific domain can be extracted using a NLP pipeline.

The presence or absence of a particular phrase can indicate which class within the domain each document should belong to. For example, by taking global phrase attention into consideration in a phrase attention layer, a HNN-GA model in accordance with several embodiments can better perform domain-specific document classification. In some such embodiments, the top phrases can serve in learning phrase-based attentions in both word and sentence levels. Additionally or alternatively, similar attention mechanisms can be used to learn important sentences and sections for classification. Furthermore, any of a variety of combination of layers within the HNN-GA can be combined to learn multiple granularities. In other words, an HNN-GA utilizing multiple granularity attention mechanisms can include more than two layers where heightened attention mechanisms are utilized and are not limited to two layers of the network model (i.e., more than two layers in the network model can include multiple granularity attention mechanisms).

In many embodiments, different words, phrases, sentences, sections, etc. in a document can be used by one or more attention mechanisms for classification. Additionally or alternatively, the different words, phrases, sentences, sections etc. can be used in training the network model to learn different weights for a classification task. A HNN-GA network model can learn weights in a training stage utilizing one or more machine learning algorithms as appropriate to the classification task in accordance with many embodiments including linear regression, logistic regression, linear discriminant analysis, principal component analysis, classification trees, regression trees, naïve Bayes, k-nearest neighbors, learning vector quantization, support vector machines, bagging forests, random forests, boosting, AdaBoost, etc. During a testing stage, a HNN-GA model can predict labels for documents and can show different weights for words, phrases, sentences, paragraphs, sections, etc. in a document. The weights can provide visualization for further understanding of classification results.

Generally, in one aspect, a method may include: obtaining data indicative of the document; processing the data indicative of the document in a first layer of two or more layers of a hierarchical network model using a dual granularity attention mechanism to generate first layer output data, wherein the dual granularity attention mechanism weights some portions of the data indicative of the document in the first layer more heavily, wherein the some portions are integrated into the hierarchical network model during training of the dual granularity attention mechanism; processing the first layer output data in the second of two or more layers of the hierarchical network model to generate second layer output data; and generating a classification label from the second layer output data. In various embodiments, the two or more layers of the hierarchical network model comprise a word layer and a sentence layer. In various embodiments, the two or more layers of the hierarchical network model further comprise a character layer, a section layer, and a document layer.

In various embodiments, the method may further include generating the classification label further includes feeding the second layer output data into a softmax function.

In various embodiments, the method may further include a dual granularity attention mechanism further including an attention history and a domain-specific attention history, wherein the attention history corresponds with the first level of the hierarchical network model and the domain-specific attention history corresponds with the second layer of the hierarchical network model. In various embodiments, the dual granularity attention mechanism is determined by the one or more processors by:

$$e_t = a(h_t, h'_t)$$
$$\alpha_t = \frac{\exp(e_t)}{\sum_{k=1}^{T} epx(e_k)}$$
$$c = \sum_{t=1}^{T} \alpha_t h_t$$

wherein e is an attention value, a is a learnable function, h is the attention history, h' is the domain-specific attention history, α is a probability vector, T is a total number of time steps, t is a time, k is a time, and c is a weighted average. In various embodiments, the domain-specific attention history is prepopulated with embeddings corresponding to knowledge in a particular domain.

In various embodiments, the method may further include the character layer further comprises a character Long Short Term Memory ("LSTM") layer wherein a character dual granularity mechanism is applied to the character LSTM layer, the word layer further comprises a word LSTM layer wherein a word dual granularity mechanism is applied to the word LSTM layer, the sentence layer further comprises a sentence LSTM layer wherein a sentence dual granularity mechanism is applied to the sentence LSTM layer, and the section layer further comprises a LSTM layer wherein a section dual granularity layer is applied to the section LSTM layer.

In addition, some embodiments include one or more processors of one or more computing devices, where the one or more processors are operable to execute instructions stored in associated memory, and where the instructions are configured to cause performance of any of the aforementioned methods. Some embodiments also include one or more non-transitory computer readable storage media storing computer instructions executable by one or more processors to perform any of the aforementioned methods.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

In the drawings, like reference characters generally refer to the same parts throughout the different views. Also, the drawings are not necessarily to scale, emphasis instead generally being placed upon illustrating various principles of the embodiments described herein.

FIG. 1B is a flowchart illustrating another example process of performing selected aspects of the present disclosure, in accordance with various embodiments.

FIG. 8A and FIG. 8B are diagrams illustrating a visual representation of sentence level and word level importance in text in accordance with various embodiments.

FIG. 9A and FIG. 9B are diagrams illustrating an additional visual representation of a sentence and word level importance in a text document using a heat map in accordance with various embodiments.

FIG. 12A and FIG. 12B are diagrams illustrating example documents a HNN-GA model correctly classified which other models failed to classify in accordance with various embodiments.

FIG. 14A and FIG. 14B are diagrams illustrating example documents incorrectly classified by a HNN-GA model in accordance with various embodiments.

FIG. 15A and FIG. 15B are diagrams illustrating example documents incorrectly classified by a HNN-GA model in accordance with various embodiments.

DETAILED DESCRIPTION

Granularized attention-based hierarchical network models ("HNN-GA") in accordance with various embodiments can encode domain level information into one or more attention mechanisms. In various embodiments, an HNN-GA can include a character layer, a word layer, a sentence layer, a section layer (sometimes referred to as a paragraph layer), and a document layer. Domain-specific information can be encoded in throughout attention mechanisms in various layers in the HNN-GA. For example, a HNN-GA network model can be used with textual radiology reports to classify if the report indicates the patient has a pulmonary embolism ("PE"). In a variety of embodiments, a HNN-GA can utilize a distinct deep learning technique such as a Recurrent Neural Network ("RNN") based model.

In many embodiments, the semantics of a specific domain (e.g., radiology reports) can be modeled through an HNN-GA composed of two or more layers including combinations of a character layer, a word layer, a sentence layer, a section layer, and/or a document layer. In some such techniques, one or more attention mechanisms can be used at one or more layers in the hierarchal network structure. In contrast to techniques which encode global user preference and product characteristics via a user-product attention mechanism for a product-oriented sentiment classification task, domain phrase attention mechanisms can encode domain dependent knowledge through a hierarchical structure.

Figure 1A:
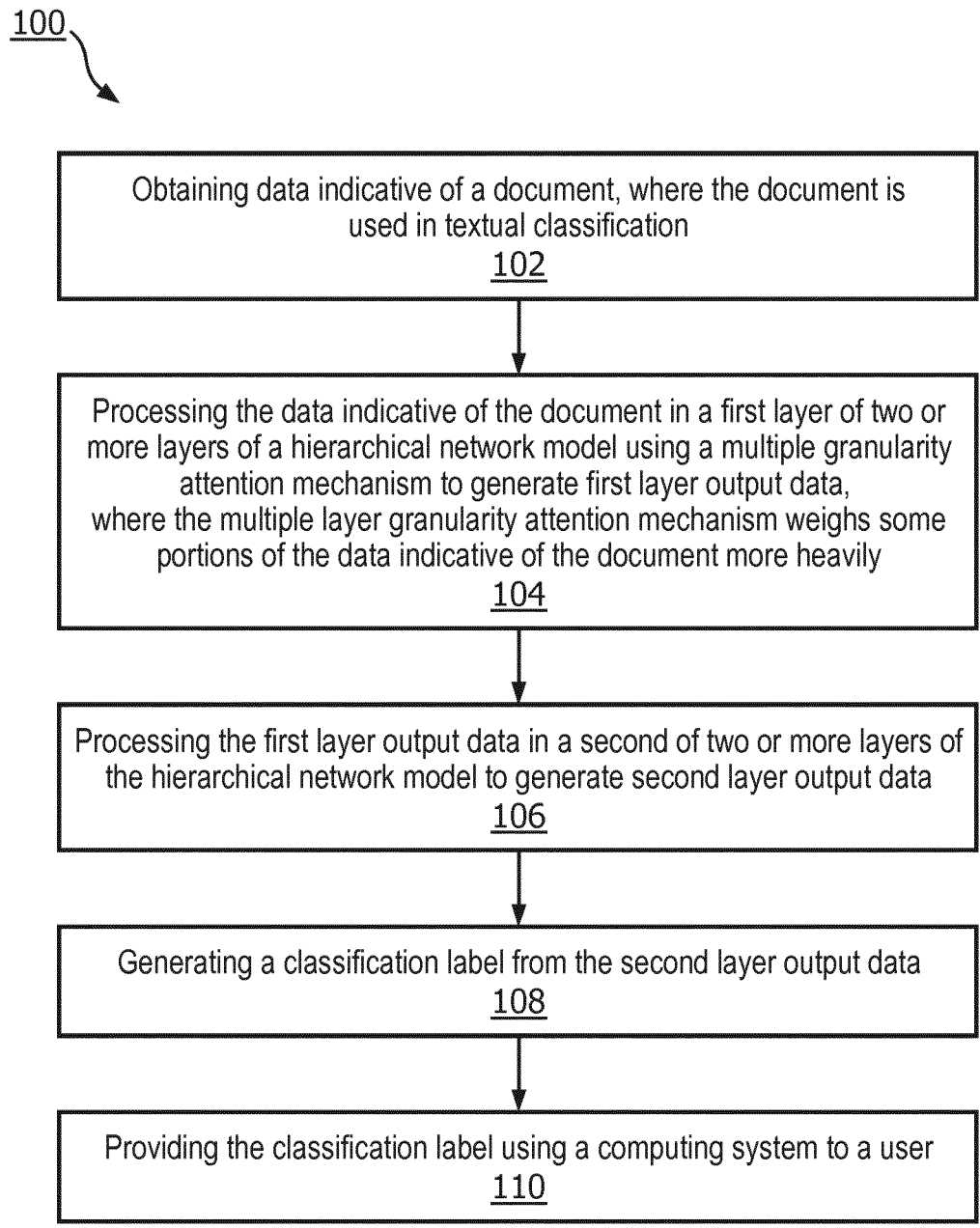
FIG. 1A is a flowchart illustrating an example process of performing selected aspects of the present disclosure, in accordance with various embodiments.

Referring to FIG. 1A, an example process 100 for practicing selected aspects of the present disclosure, in accordance with many embodiments, is disclosed. For convenience, the operations of the flowchart are described with reference to a system that performs the operations. This system may include various components of various computing systems, including those described in FIG. 16. Moreover, while operations of process 100 are shown in a particular order, this is not meant to be limiting. One or more operations may be reordered, omitted, and/or added.

At block 102, data indicative of a document can be obtained. In some embodiments, a document can be character representations of a textual document which can be classified by a HNN-GA. For example, the document can be a radiology report which can be classified to identify if it contains information relating to a PE or other medical conditions.

At block 104, the data indicative of the document can be processed in a first layer of two or more layers of a hierarchical network model using a multiple granularity attention mechanism to generate first layer output data. In a variety of embodiments, the two or more layers of the hierarchical network model can include a character layer, a word layer, a sentence layer, a section layer (sometimes referred to as a paragraph layer), a document layer, etc. In some embodiments, one or more layers can additionally include a Long Short Term Memory ("LSTM") network. The multiple granularity attention mechanism can weigh some portions of the data indicative of the document more heavily than others. In other words, some portions of the data can receive heightened attention from an attention mechanism; other portions of the data can receive reduced attention from the attention mechanism. For example, HNN-GA configured with selected aspects of the present disclosure can include a word layer, a sentence layer, and/or a document layer. Each layer within an HNN-GA configured with selected aspects of the present disclosure may include one or more attention mechanisms. An attention mechanism within the multiple granularities of attention mechanisms in a layer of a HNN-GA in accordance with several embodiments can be prepopulated with domain words/phrases extracted using a NLP engine.

At block 106, the first layer of output data can be processed in a second of two or more layers of the HNN-GA to generate second layer output data. As described above at block 104, the two or more layers of the HNN-GA can include a character layer, a word layer, a sentence layer, a section layer (sometimes referred to as a paragraph layer), a document layer, etc.

At block 108, a classification label can be generated from the second layer output data. In many embodiments, a softmax function can be used to generate the classification label. In a radiology report example, classification labels can include class labels, for example {PEpositive, PEnegative} (which can indicate the presence or absence of a pulmonary embolism), {PEacute, PEchronic} (which can indicate if an identified pulmonary embolism is acute or chronic), etc.

At block 110, the classification label can be provided to a user using a computing system. In some embodiments, as illustrated in FIGS. 8A-9B below, a visual representation of the weights assigned to portions of a textual document can be provided with the classification label to the user which emphasizes one or more levels of attention.

FIG. 1B illustrates an example process 150 for practicing selected aspects of the present disclosure, in accordance with many embodiments. For convenience, the operations of the flowchart are described with reference to a system that performs the operations. This system may include various components of various computing systems, including those described in FIG. 16. Moreover, while operations of process 150 are shown in a particular order, this is not meant to be limiting. One or more operations may be reordered, omitted, and/or added.

At block 152, data indicative of a character representation of a document in a character layer of a hierarchical network model can be processed using a character multiple granularity attention mechanism to generate data indicative of a word representation. As described above in block 104, a multiple (e.g., dual) granularity attention mechanism can give greater weight to some portions of the data than others. At block 154, data indicative of a word representation in a word layer of the hierarchical network model can be processed using a word multiple granularity attention mechanism to generate data indicative of a sentence representation. At block 156, data indicative of a sentence representation in a sentence layer of the hierarchal network model can be processed using a sentence multiple granularity attention mechanism to generate data indicative of a section representation.

At block 158, data indicative of a section representation in a section layer of the hierarchical network model can be processed using a section multiple granularity attention mechanism to generate data indicative of the document.

At block 160, a document classification label can be processed from the data indicative of the document. At block 162 the document classification label can be provided to one or more users using a computing system. As described in block 110 above, a visual representation of the textual document can be provided to the user based on the classification label.

Figure 2:
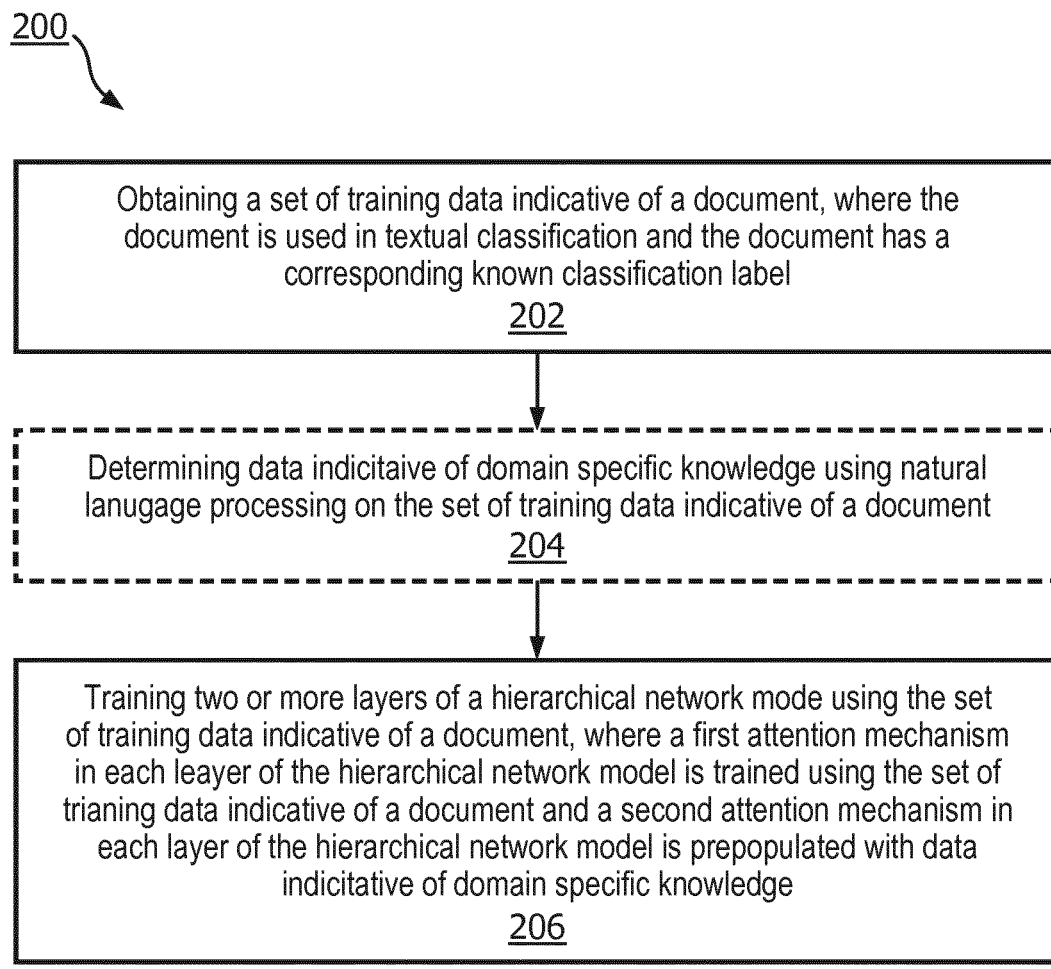
FIG. 2 is a flowchart illustrating another example process of performing selected aspects of the present disclosure, in accordance with various embodiments.

FIG. 2 illustrates an example process 200 for practicing selected aspects of the present disclosure—namely, training an HNN-GA—in accordance with many embodiments. For convenience, the operations of the flowchart are described with reference to a system that performs the operations. This system may include various components of various computing systems, including those described in FIG. 16. Moreover, while operations of process 200 are shown in a particular order, this is not meant to be limiting. One or more operations may be reordered, omitted, and/or added.

At block 202, a set of training data indicative of a document for use in textual classification can be obtained. This set of training data includes the text of a document (for example, the text can be represented in a character format) as well as a corresponding known classification label for the document. In various embodiments, a set of training data can include data indicative of many documents. However, it is undesirable if the model learns to classify the training data set and is unable to correctly classify unknown data (sometimes referred to as overfitting). Therefore, in many embodiments, the set of training data is carefully selected to find a balance between teaching the network model to generate accurate classification labels for the known data in the training set with selecting a training set that will train the network model to generate accurate classification labels for unknown data in the future. In some such embodiments, a first set of training data with a known classification label can be used to train a network model and a second set of known training data with a known classification label (sometimes referred to as a testing data set) can test the accuracy of the network model. This second set of training data (or testing data) can confirm the accuracy of the classification of the network model. Additionally or alternatively, a "better" set of training data can be selected to train a network model that is poorly generating classification labels of a testing data set.

At block 204, data indicative of domain-specific knowledge can optionally be determined using natural language processing on the set of training data indicative of a document. Domain-specific knowledge can relate to a specific classification task. For example, domain-specific knowledge for a classification task of labeling radiology reports indicating a pulmonary embolism can include the phrase "pulmonary embolism", the individual words "pulmonary", "embolism" or other clinical concepts that are typically represented in a medical ontology. Other general domain cue words like "not present" or individually "not", "present" etc. can also help classifying the documents. Furthermore, different domain-specific knowledge can be extracted for different levels of a HNN-GA. For example, a set of domain knowledge for one layer within a HNN-GA can include words while a different set of domain knowledge can include phrases.

In other embodiments, domain knowledge for a HNN-GA can be predetermined. In other words, the domain-specific knowledge is not extracted from a set of training data indicative of a document but is instead drawn from a previously known set of data. Additionally or alternatively, a previously known set of data can be combined with data indicative of domain-specific knowledge extracted from the set of training data using natural language processing techniques. In many embodiments, domain-specific knowledge (previously known and/or extracted from a set of training data) can prepopulate an attention mechanism in a layer of a HNN-GA. For example, in dual attention mechanisms, the second attention mechanism can be prepopulated with domain-specific knowledge so the HNN-GA can pay heightened attention to relevant domain knowledge when generating a classification label for input data.

At block 206, two or more layers of the HNN-GA can be trained using the set of training data indicative of a document. In many embodiments, the HNN-GA can be trained using a set of training data using backpropagation. Backpropagation can include calculating weights within the HNN-GA using a set of training data to generate a classification label and comparing the generated classification label with the known classification label for the training data (i.e., propagating the training data through the network). The weights for each layer in the HNN-GA (and/or individual neurons within each layer in the network model), can be updated based on the difference between the generated classification label and the known classification label, and these updated weights can be distributed back through the HNN-GA (i.e., weight updating).

In many embodiments, a first attention mechanism within one or more layers of a HNN-GA can be trained using a set of training data. In some embodiments, a set of training data can be used to train multiple attention mechanisms within a single layer of a HNN-GA. In other embodiments, a second attention mechanism can be prepopulated with domain-specific knowledge (such as a set of predetermined knowledge and/or domain-specific knowledge extracted from the training set in optional block 204).

Figure 3:
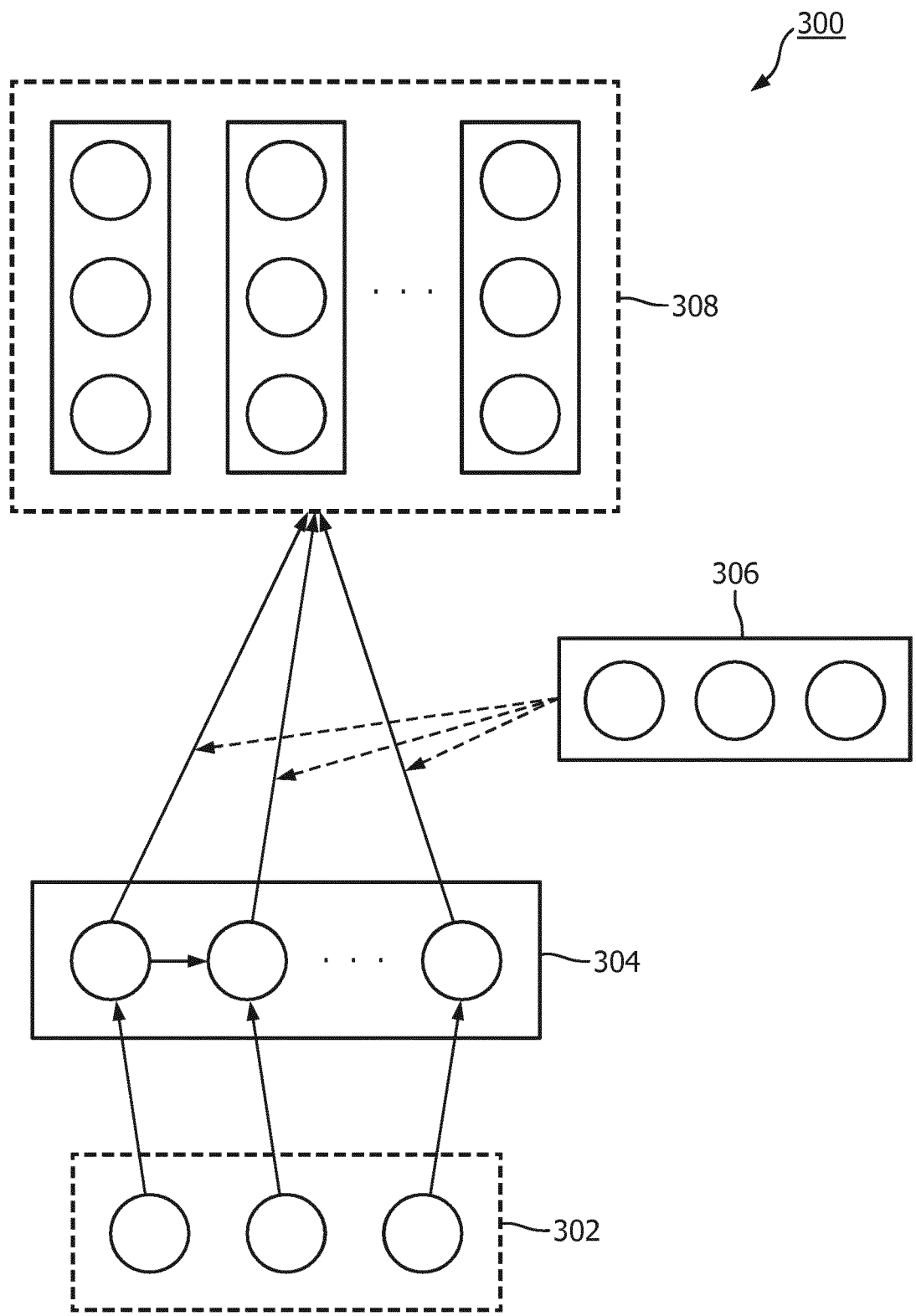
FIG. 3, FIG. 4, FIG. 5 and FIG. 6 are diagrams illustrating an example of a neural network model in accordance with various embodiments.

FIG. 3-FIG. 6 illustrates an HNN-GA in accordance with many embodiments. In some such embodiments, FIG. 3-FIG. 6 illustrate a downstream classification task for textual classification using a dual granularity attention mechanism. In other words, two layers of granularity are used for attention mechanisms as illustrated in FIG. 3-FIG. 6. However, this is not meant to be limiting and additional attention mechanisms can be used as appropriate to many embodiments. As an illustrative example using radiology reports, the input to a network model in accordance with some embodiments can be a radiology report. The output classification label can include a variety of radiology related labels such as "Pulmonary embolism present", "Pulmonary embolism absent", "pulmonary embolism acute" etc. FIG. 3 illustrates image 300 which illustrates an example of a character layer of a hierarchical network. Image 300 contains a character representation 302 of a textual document. Character representation 302 can be passed to a character layer LSTM 304. A character layer attention mechanism 306 can be applied to the output of the output of character LSTM layer 304, which can generate a word representation 308 for use in a word layer. In many embodiments, a character layer attention mechanism 306 can learn additional weights to denote which characters are more important in the current representations such that these features can be used while predicating a class label in the output.

Figure 4:
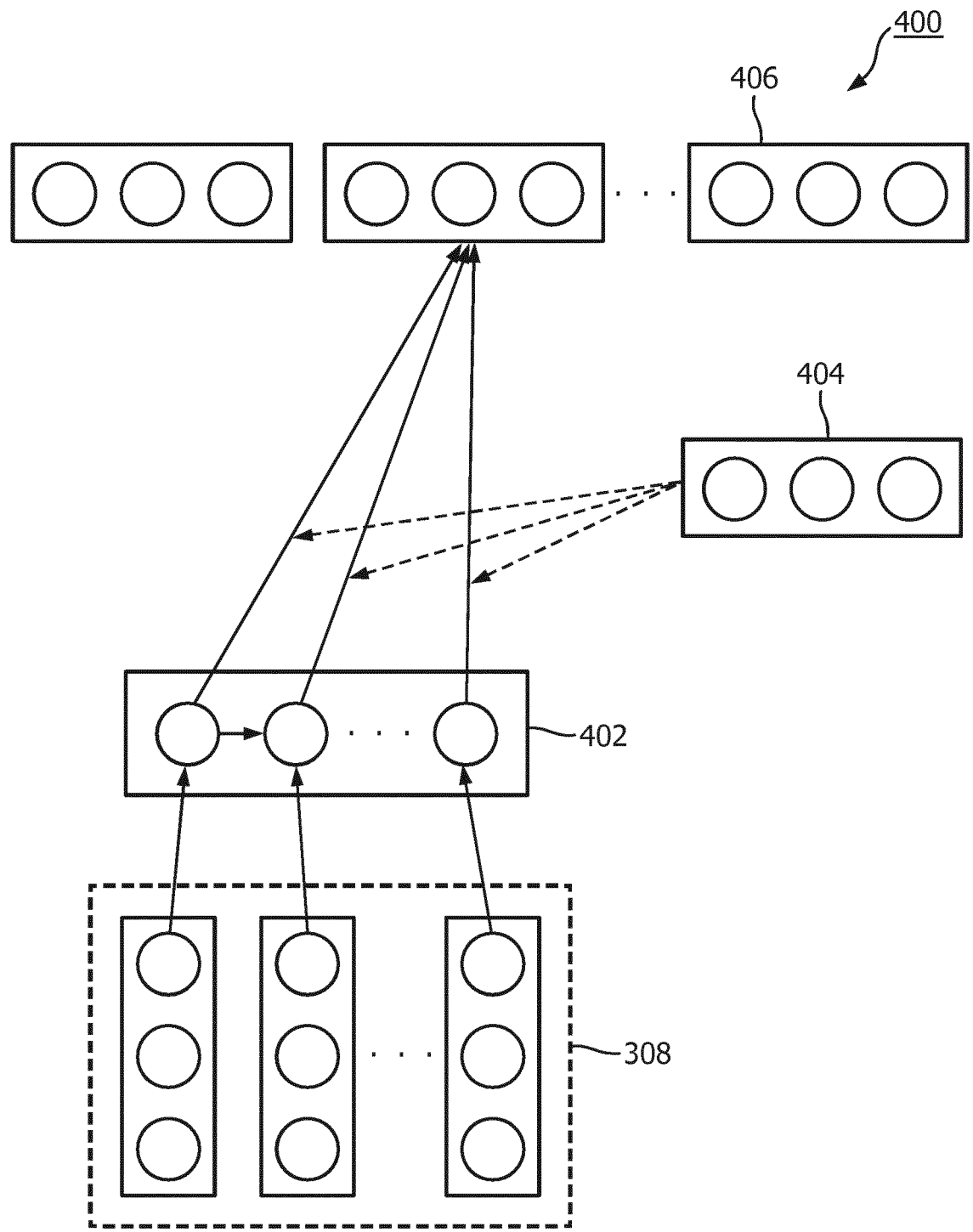

FIG. 4 illustrates image 400 which illustrates an example of a word representation layer of an HNN-GA configured with selected aspects of the present disclosure. Image 400 contains a word representation 308 of the textual document similar to that generated by a word layer described in FIG. 3. In some embodiments, each word can be represented by a vertical box including multiple circles, where each circle can denote a character representation. The word representation can be passed as input to a word layer LSTM 402. A word layer attention mechanism 404 can be applied to the output of word layer LSTM unit 402 which can generate a sentence representation 406 of the textual document. In many embodiments, a word layer attention mechanism 404 can be used to learn additional weights of the words which are important in predicting a class label in the output.

Figure 5:
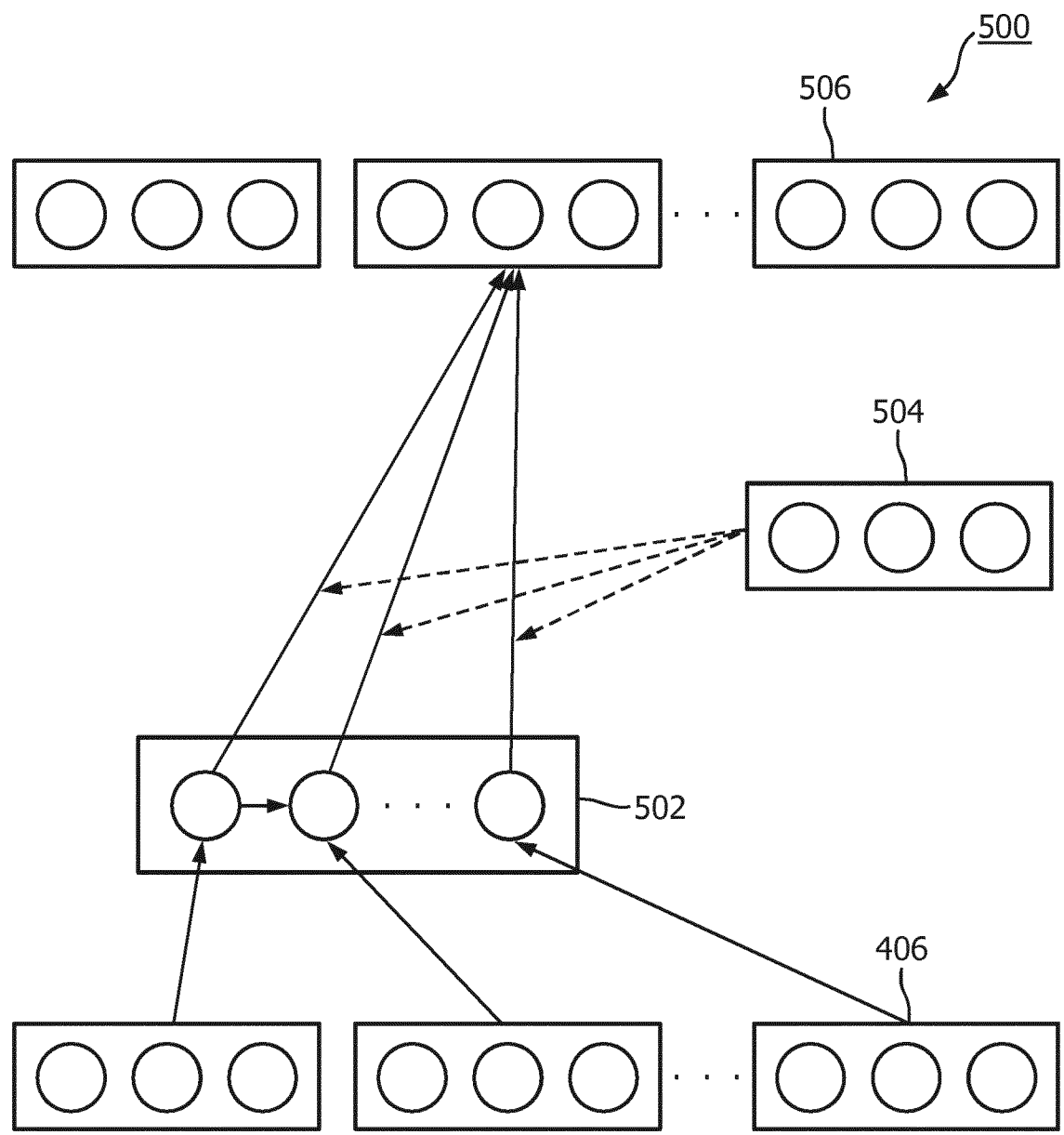

FIG. 5 illustrates image 500 which illustrates an example of a sentence representation layer of an HNN-GA configured with selected aspects of the present disclosure. Image 500 contains a sentence representation 406 of the textual document which can be generated by a sentence representation layer described in FIG. 4. In some embodiments, sentence representation 406 can indicate a series of boxes each indicating a word with characters of the words denoted as circles within each box. It should be readily appreciated that three character words as illustrated in sentence representation 406 is merely illustrative and words can have any varying number of characters. The sentence representation can be passed as input to a sentence layer LSTM 502. A sentence layer attention mechanism 504 can be applied to the output of the sentence layer LSTM unit 502 to generate a section representation 506 of the textual document. In a variety of embodiments, a sentence layer attention mechanism 504 can be used to learn additional weights of the sentences which are important in predicting a class label in the output.

Figure 6:
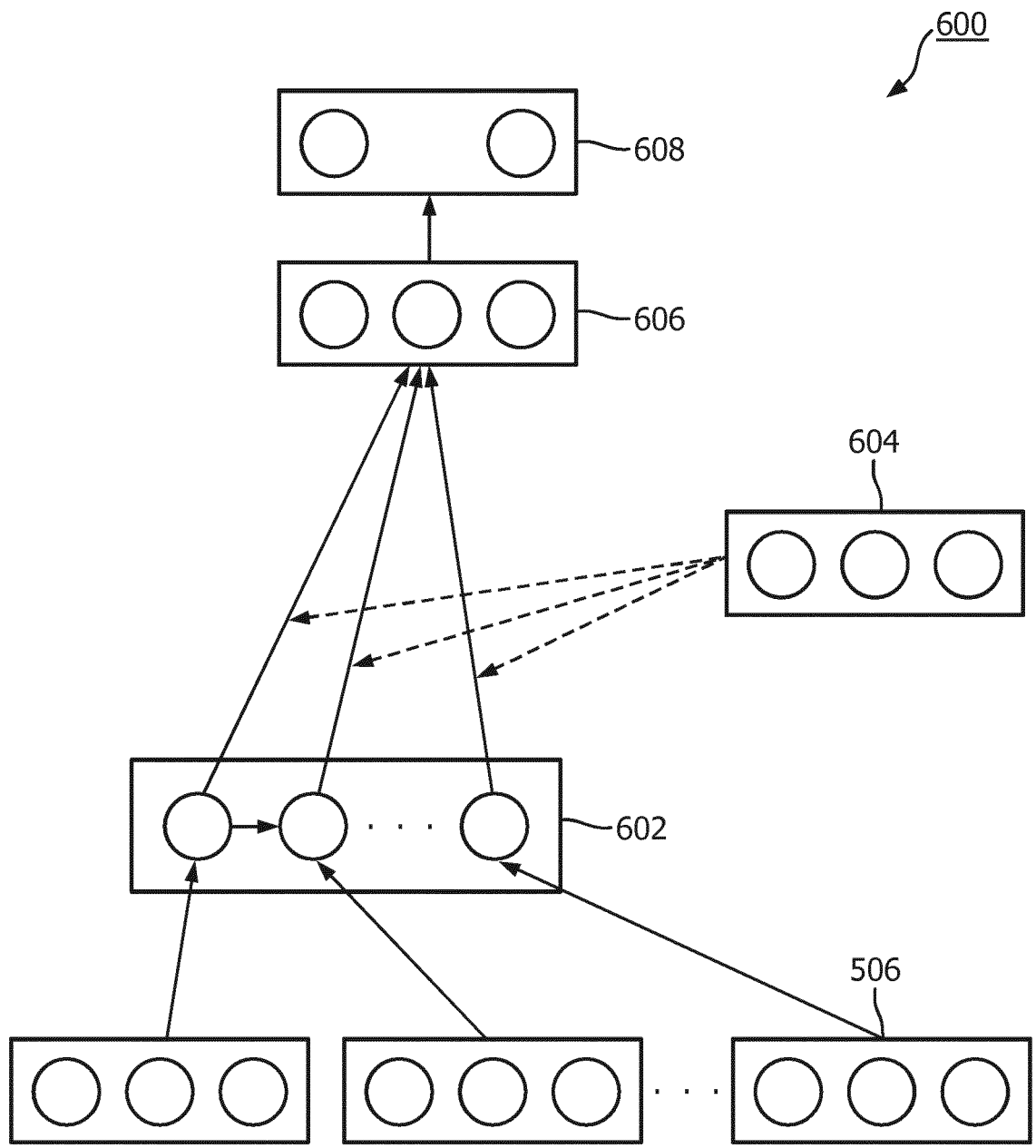

FIG. 6 illustrates image 600 which illustrates an example of a section representation layer of an HNN-GA configured with selected aspects of the present disclosure. Image 600 contains a section representation 502 of the textual document which can be generated by a sentence representation layer described in FIG. 5. A section representation 502 can include a combination of words, each represented by boxes with circles denoting characters of each word. As described above, the use of three character words is merely an illustrative example and words can have any of a variety of number of characters are required by each word. In many such embodiments, section representations can include a combination of many sentences. The section representation 506 can be passed as input to a section layer LSTM 602. A section layer attention mechanism 604 can be applied to the output of the section layer LSTM 602 to generate a document representation 606 of the textual document. In some embodiments, a section layer (as well as its corresponding components) can also be referred to as a paragraph layer. In a variety of embodiments, the section layer attention mechanism 604 can learn additional weights of sections which are important in predicting the classification of a label for the input document. The document representation 606 can be passed to a classification function 608 to generate a classification label. In many embodiments, a classification function can be a softmax function.

Figure 7:
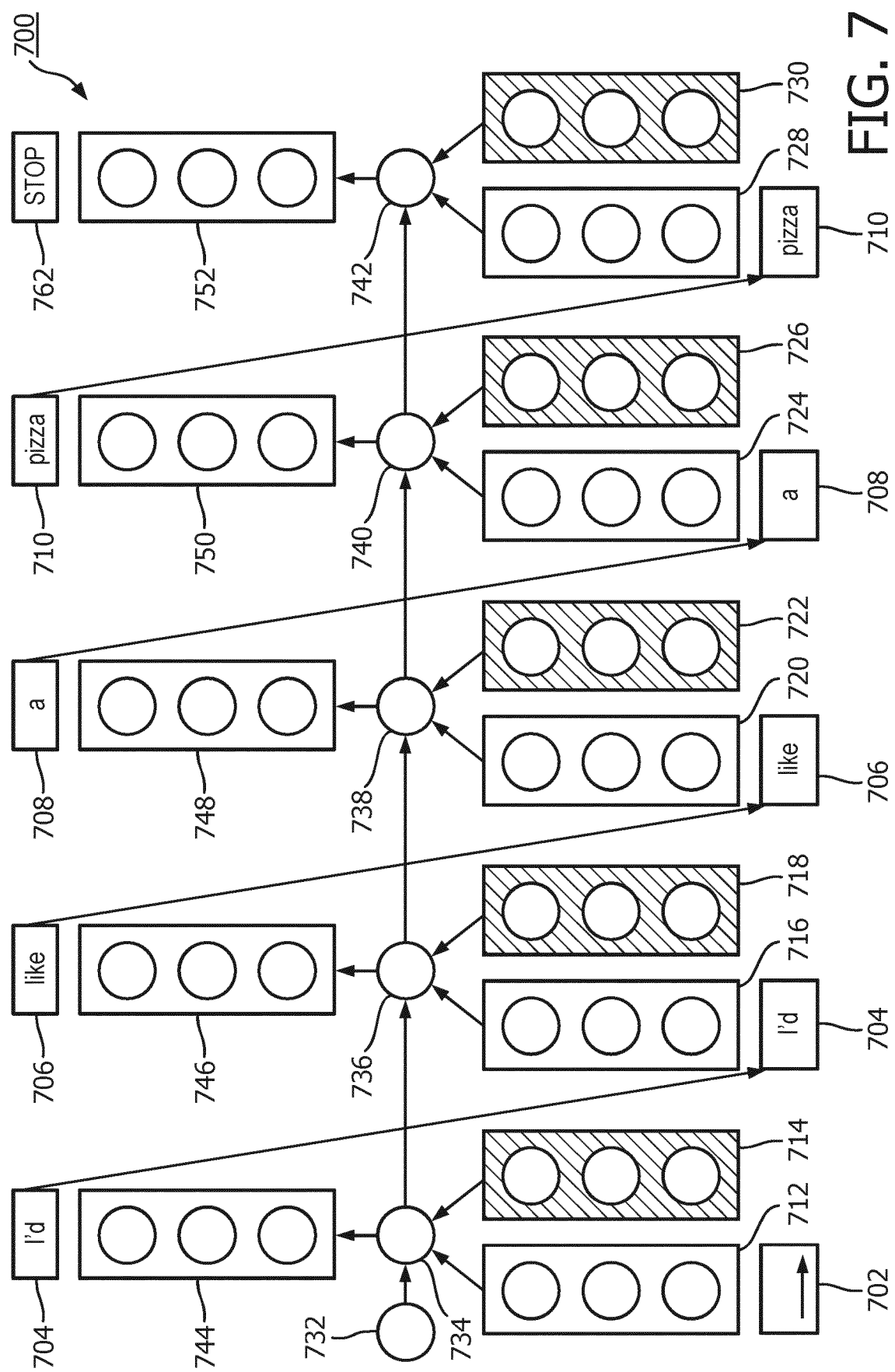
FIG. 7 is a diagram illustrating an example of an attention mechanism in accordance with various embodiments.

FIG. 7 illustrates an attention mechanism in accordance with many embodiments. One or more levels of the HNN-GA in accordance with many embodiments can include a dual granularity attention mechanism. For example, a sentence layer in a HNN-GA can include a dual granularity attention mechanism that can consider both sentences and phrases for heightened attention. In some such embodiments, an additional attention history can be maintained and populated with terms in a second granularity level. For example, if the first level of attention is sentence level, the second granularity can be phrase level. A new attention history $h_t'$ can be populated with phrase embeddings. The second attention history $h_t'$, while not necessarily associated with additional hidden layers in some embodiments, can cause the model to pay attention to this additional granularity and affect the weight value for each hidden layer. In some embodiments, these can be domain phrases for the particular application of the HNN-GA. For example, when the HNN-GA is used to interpret radiology reports, the domain phrases may include phrases such as "pulmonary embolism", "no evidence of deep thrombosis", etc.

In a variety of embodiments, a first granularity of attention history $h_t$, and a second granularity of attention history $h_t'$ can be used to determine a dual granularity attention mechanism using the following expressions:

$$e_t = a(h_t, h_t') \tag{1}$$

$$\alpha_t = \frac{\exp(e_t)}{\sum_{k=1}^{T} epx(e_k)} \tag{2}$$

$$c = \sum_{t=1}^{T} \alpha_t h_t \tag{3}$$

where e in an attention value, a is a learnable function, h is the first granularity attention history, h' is the second granularity attention history (which in a variety of embodiments can be a domain-specific attention history), α is a probability vector, T is a total number of time steps, t is a time, k is a time, and c is a weighted average.

As illustrated in image 700, an input sentence "I'd" 704, "like" 706, "a" 708, "pizza" 710 can be received as input to a dual granularity attention mechanism. In a variety of embodiments, a specialized word, phrase, character representation etc. such as "STOP" 762 can indicate the end of a sentence. In a variety of embodiments, similar indicators can be used between characters in a document, between words in a document, between sections in a document etc. depending on the layer of the HNN-GA network model.

A first granularity attention history 712, 716, 720, 724, 728 and a second granularity attention history 714, 718, 722, and 730 can be applied to the input sentence. In a variety of embodiments, first granularity attention history 712 and second granularity attention history 714 can receive input 702 from previous sentences in a sentence layer of an HNN-GA, and this previous input can be indicated by an arrow. Additionally or alternatively, depending on the layer of the HNN-GA, input 702 can represent previous characters, words, sections, etc. In many embodiments, first granularity attention history 716 and second granularity attention history 718 can receive the input word "I'd" 702 from the input sentence. Similarly, a first granularity attention history 720 and second granularity attention history 722 can receive the input word "like" 706. Furthermore, first granularity attention history 722 and second granularity attention history 724 can receive the input word "a" 708. Additionally or alternatively, first granularity attention history 728 and second granularity attention history 730 can receive the word "pizza" 710 as input. The output of first granularity attention histories and second granularity attention histories are combined in elements 734, 736, 738, 740, and 742. Elements 734, 736, 738, 740, and 742 can combine the output of a first granularity attention history and a second granularity attention history in a variety of ways including concatenating the attention histories, subtracting one attention history from the other, multiplying the attention histories, etc.

In a variety of embodiments, the output of first granularity attention history 712 and the output of second granularity attention history 714 can be combined in element 734. Additionally or alternatively, information from a previous iteration 732 can be passed as additional input to element 734 (i.e., in addition to the output from first attention history 712 and second attention history 714). The output of element 734 is an output attention history 744. In many embodiments, the output of attention history 744 can be applied to a corresponding portion in a LSTM to generate the representation of the next layer in the HNN-GA. In a word layer as illustrated in image 700, the output attention histories 744, 746, 748, 750, and 752 can be applied to the word layer LSTM to generate a sentence representation.

The output of first granularity attention history 716 and the output of second granularity attention history 718 can be combined in element 736 to. Element 736 can also receive input from element 734 (i.e., information from a previous word can be passed to the next word when generating attention history outputs). In a variety of embodiments, the output of element 736 can generate an output attention history 746, which as described above can be applied to the LSTM of the corresponding layer of the HNN-GA. Similarly, the output of first granularity attention mechanism 720 and the output of second granularity attention mechanism 722, and element 736 can be combined in element 738 to generate output attention history 748. The output of first granularity attention mechanism 724 and the output of second granularity attention mechanism 726 can be combined with the output of element 738 in element 740 to generate output attention history 750. Additionally or alternatively, the output of first granularity attention history 728 and the output of second granularity attention history 730 can be combined with the output of element 740 in element 742 to generate output attention history 752.

FIGS. 8A and 8B illustrate a visual representation of heightened attention given to information in a textual document at a word and sentence level. Image 802 in FIG. 8A illustrates a textual document which has been classified to have a positive PE label. Similarly, Image 850 in FIG. 8B illustrates a textual document which has been classified to have a negative PE label. In both FIGS. 8A and 8B, words and/or phrases with heightened attention during classification are indicated in italicized text. Additionally or alternatively, words with an even greater weight are further indicated as italicized bold text. For example, in sentence 2 of FIG. 8A, "patchy consolidation" is indicated to have a higher importance by being italicized. Furthermore, "consolidation" has a higher importance compared to "patchy" so "consolidation is additionally bold. Similarly, sentences with heightened attention are indicated by underlining the sentence number. For example, sentences 3 and 4 are underlined in FIG. 8B to indicate those sentences have a higher sentence level importance.

Figure 9B:
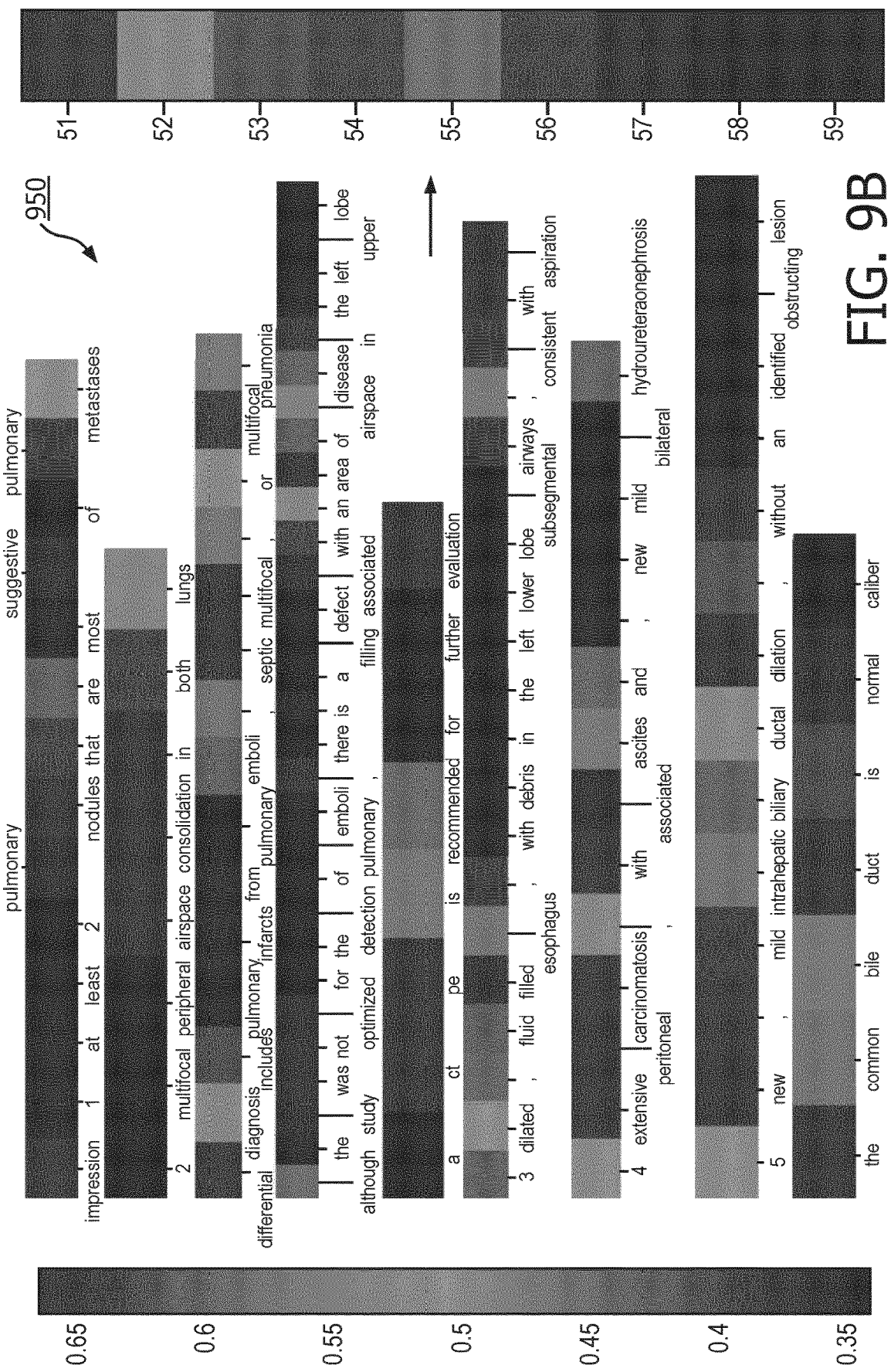

FIGS. 9A and 9B illustrate an additional visual representation of heightened attention given to information in a textual document at a word and sentence level. Image 902 in FIG. 9A illustrates a "Sample Report" textual document which has been divided into nine sentences. Image 950 in FIG. 9B illustrates a corresponding heat map generated by the weighted attention given to words and sentences in "Sample Report" as illustrated in FIG. 9A.

In a variety of embodiments, HNN-GA models can be specialized for a specific domain such as interpreting radiology reports. Additionally or alternatively, as discussed above, HNN-GA models can include a variety of layers and layers utilized in several embodiments can be specialized. In various embodiments, the semantics of a radiology report can be modeled through a hierarchical structure composed of word-level, sentence-level and document-level representations. A Domain Phrase Attention-based Hierarchical Neural Network model ("DPA-HNN") (also referred to as a HNN-GA as illustrated in FIGS. 3-6 above) can encode clinical domain-dependent phrases into an attention mechanism and represent a radiology report through a hierarchical structure composed of word-level, sentence-level and document-level representations. In many embodiments, compared to a simple attention mechanism such as using word attention, domain phrase attention can play a more important role in classifying radiology reports as radiologists traditionally follow a domain-specific note writing style. Moreover, some domain phrases occur frequently in radiology documents, justifying a DPA-HNN model with a domain phrase attention mechanism.

While a Recurrent Neural Network ("RNN") model is a powerful model which can encode sequential information in accordance with embodiments, it can suffer from the vanishing/exploding gradient problems while learning long-range dependencies. Long Short Term Memory ("LSTM") network models and Gradient Recurrent Units ("GRU") network models are known to typically be successful remedies to these problems. In various embodiments, LSTM models can be utilized. However, in other embodiments GRU units can replace LSTM units. In many embodiments, LSTM can be utilized as the hidden layer activation unit to model the semantic representations of sentences and documents. In various embodiments, each cell in a LSTM is computed as follows:

$$X = \begin{bmatrix} h_{t-1} \\ x_t \end{bmatrix} \quad (4)$$

$$f_t = \sigma(W_f \cdot X + b_f) \quad (5)$$

$$i_t = \sigma(W_i \cdot X + b_i) \quad (6)$$

$$o_t = \sigma(W_o \cdot X + b_o) \quad (7)$$

$$c_t = f_t \odot c_{t-1} + i_t \odot \tanh(W_c \cdot X + b_c) \quad (8)$$

$$h_t = o_t \odot \tanh(c_t) \quad (9)$$

where $W_i$, $W_f$, $W_o \in \mathbb{R}^{d \times 2d}$ are the weight matrices and $b_i$, $b_f$, $b_o \in \mathbb{R}^d$ are the biases of LSTM to be learned during training, parameterization, and transformations of the input, forget and output gates, respectively. In various embodiments, σ is the sigmoid function and ⊙ stands for element-wise multiplication. Additionally or alternatively, $x_t$ is the input of a LSTM cell unit and $h_t$ represents the hidden state at time t.

In various embodiments it can be assumed that a document has L number of sentences, where each sentence $s_i$ contains $T_i$ words. Furthermore, $w_{it}$ with t∈[1, T] can represent the words in the ith sentence. For word-level computations, $x_t$ can represent the word embedding vectors $w_t$. The first hidden layer vectors $h_{it}$ with t∈[1, T] can be used to represent a sentence. For sentence-level computations, $x_t$ represents the sentence embedding vectors $s_i$. The hidden layer vectors $h_i$ with i∈[1, L] can be used to represent a document in this case.

The last hidden layer can be the representation of a document and a softmax layer can be placed on top of the last hidden layer to predict classification labels e.g. $\{PE_{Positive}, PE_{Negative}\}$ or $\{PE_{Acute}, PE_{Chronic}\}$ for the radiology report. In various embodiments, considering h* as the final representation of a radiology report, the softmax layer can be formulated as:

$$y = \text{softmax}(W_s h^* + b_s) \quad (10)$$

where $W_s$ and $b_s$ are the parameters of the softmax layer. The negative log likelihood of the correct labels can be used as a training loss function:

$$L = \Sigma_d \log y_{dj} \quad (11)$$

where j is the label of a document d.

In contrast, hierarchical neural network (I-INN) models without attention, can feed the hidden states to an average pooling layer to obtain the sentence representation and the final document representation. For example, the final feature representation of a radiology report can be computed as:

$$h^* \Sigma_{i \in [1,L]}^i h_i \quad (12)$$

A domain phrase attention mechanism in accordance with many embodiments can capture the most important part of a document and essentially of a sentence by taking domain phrases into consideration. It can be reasonable to reward sentences that are clues to correctly classify a document. Hence, extra attention can be paid to domain phrases if they are present in a sentence. Each domain phrase can be encoded as continuous and real-valued vectors $p \in \mathbb{R}^d$, which can be randomly initialized. This yields:

$$u_i = \tanh(W_s h_i + W_{dp} p + b_s) \quad (13)$$

$$\alpha_i = \frac{\exp(u_i^T u_s)}{\Sigma_i \exp(u_i^T u_s)} \quad (14)$$

$$h^* = \sum_{i \in [1,L]}^i \alpha_i h_i \quad (15)$$

where $W_s$ and $W_{dp}$ are projection parameters and $b_s$ is the bias parameter to be learned during training.

Figure 10:
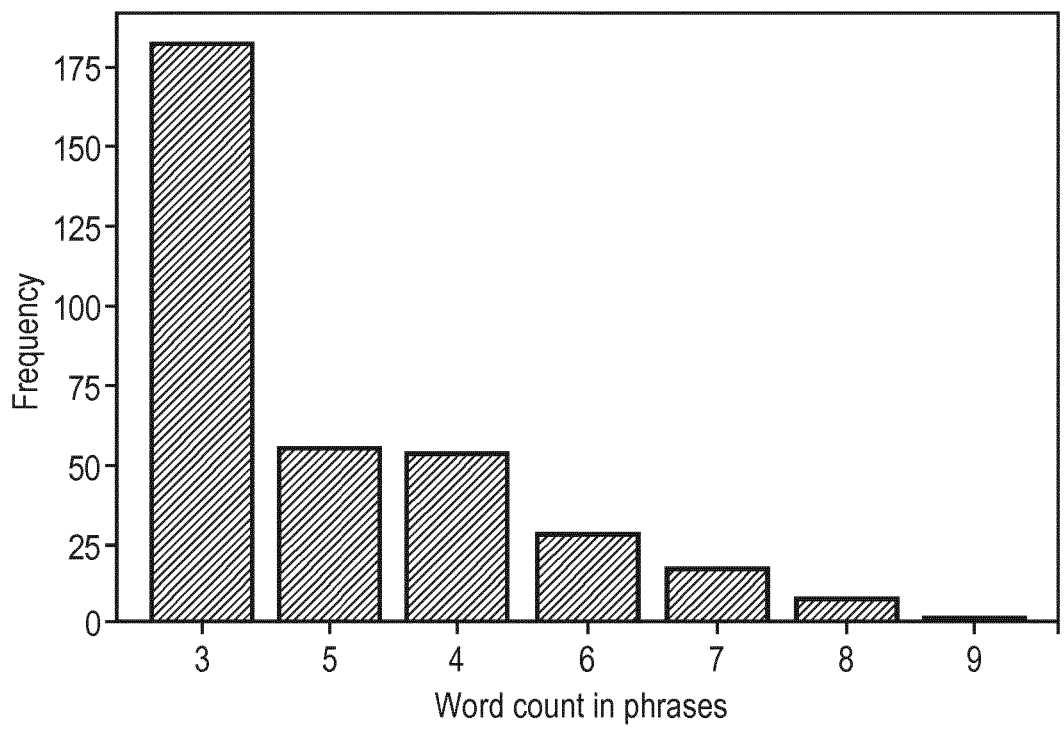
FIG. 10 is a diagram illustrating the frequency distribution of word counts in domain phrases and domain phrase examples in accordance with various embodiments

In some embodiments, clinical concepts can be extracted from the radiology reports based on SNOMED Clinical Terms ontology (i.e., a systematically organized collection of medical terms which can be used in clinical documenting and reporting) using a hybrid clinical Natural Language Processing ("NLP") engine. The consecutive clinical concepts occurred in the same sentence can be combined as one domain phrase. For example, in the sentence "three small low attenuation lesions within the liver, which are too small to characterize", "low attenuation" and "lesions" can be tagged as two separate clinical concepts by the clinical NLP engine. However, since they are consecutive words in the sentence, the words can be regarded as the domain phrase "low attenuation lesions". In other words, the clinical concepts should be consecutively present in sentence in order to be the part of a domain phrase. The list of Domain Phrases (DPs) is generated from the Stanford training set. The total number of DPs in the Stanford training set is 343, and the average number of words in DPs is approximately equal to 4. The frequency distribution of word counts in DPs and DP examples in accordance with various embodiments are illustrated in image 1000 of FIG. 10.

The performance of DPA-HNN (also referred to as HNN-GA) models can be tested on a variety of data sets including radiology specific data sets such as: Stanford, UPMC, Colorado Childrens, Duke, etc. using one or more of the following metrics: Precision, Recall, F1 value, Area Under the Curve (AUC), etc. In order to convert the predicted probability values of neural models to binary class labels, optimal cutoff threshold can be determined of the probability of the positive class by maximizing: Precision($t_i$)+Recall($t_i$) for all the thresholds ($t_i$) between 0 to 1.

With respect to the Stanford test set, DPA-HNN has the best scores on all evaluation metrics for both PE Positive/Negative and PE Acute/Chronic classifications. Compared with Hierarchical Neural Network (HNN) models and Attention-based Hierarchical Neural Network (A-HNN) models, a DPA-HNN model encoding domain phrase attention can improves the performance of the DPA-HNN network model. In various embodiments, the improvements of DPA-HNN model over a HNN model and an A-HNN model were found to be statistically significant (p<0.05). From the results it can be seen that typically, neural network-based methods have better performance than the classic PEFinder, Support Vector Machine (SVM), and/or Adaboost methods in term of F1 and AUC scores on Stanford test set.

Additionally, with respect to the UPMC dataset, DPA-HNN has the best precision scores for both tasks. Furthermore, with respect to the Duke test set, DPA-HNN has the best AUC scores for both tasks. Additionally or alternatively, with respect to the Colorado Childrens test set, HNN has the best scores on all evaluation metrics for PE Positive/Negative classification, while not performing well on PE Acute/Chronic classification.

Figure 11A:
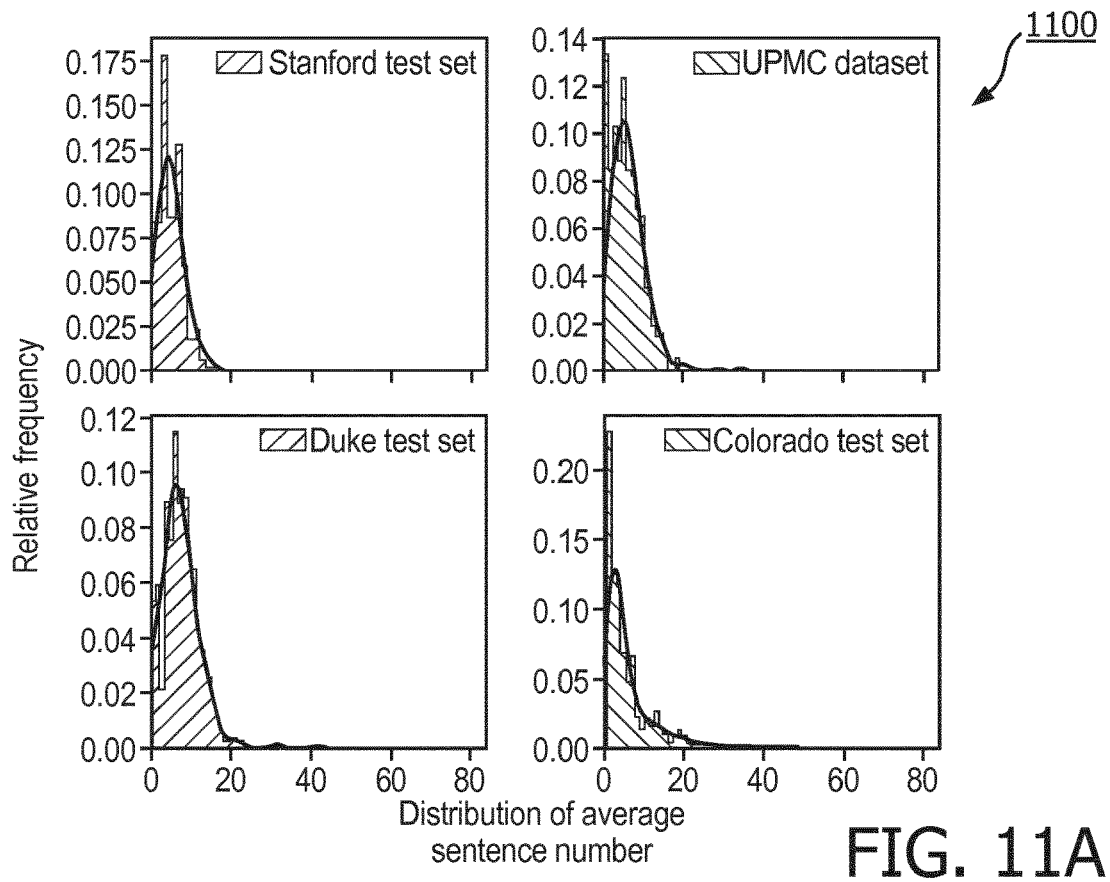
FIG. 11A and FIG. 11B are diagrams illustrating the distribution of average sentence number and average domain phrases number in various testing datasets in accordance with various embodiments.
Figure 11B:
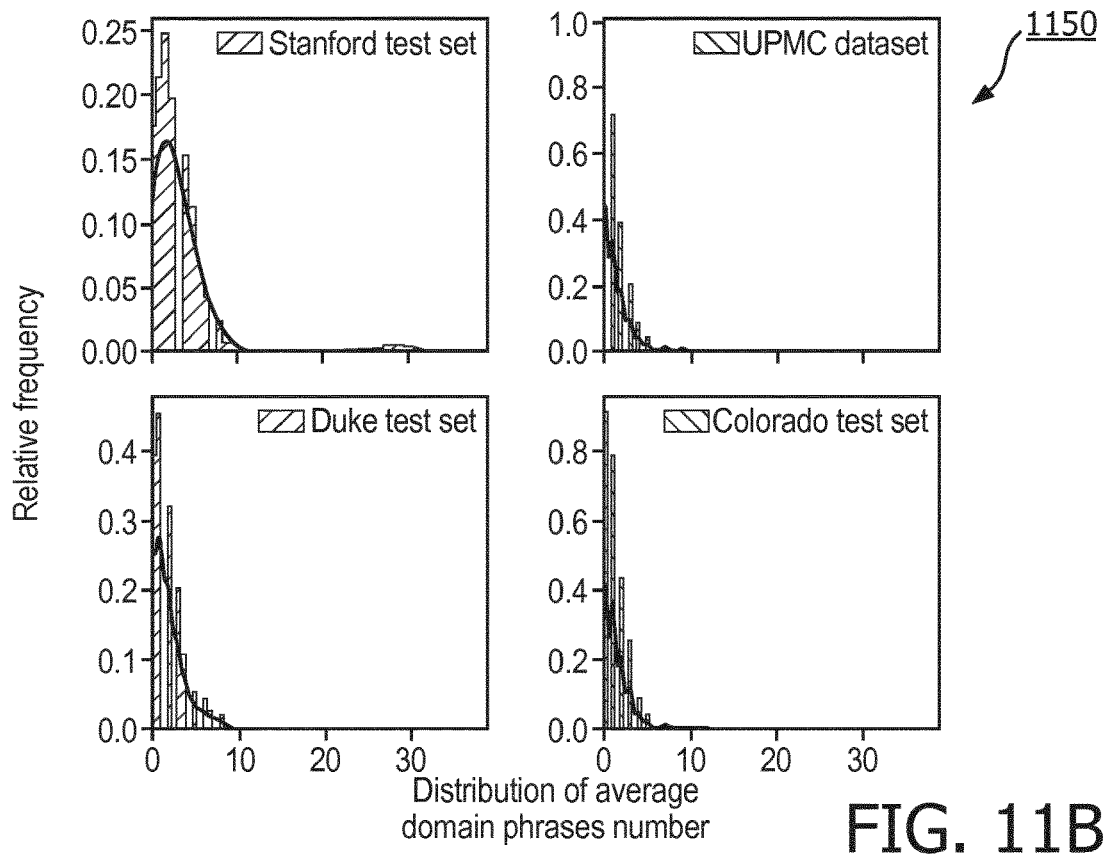

Overall, DPA-HNN models in accordance with many embodiment can show performance improvement on the Stanford test set, and partially on the UPMC dataset and the Duke test set. While DPA-HNN performed lower on the Colorado Childrens test set, the DPA-HNN and other neural network based models are trained on the Stanford dataset comprising mostly adult patients (in contrast to the specific pediatric population of the Colorado Childrens test set). Further analyses revealed that the external datasets (UPMC dataset, Duke test set, Colorado Childrens test set) have varying distributions of average number of sentences and domain phrases in a document. The distributions and statistics are illustrated in FIGS. 11A-11B and the table below. Image 1100 of FIG. 11A illustrates the distribution of average sentence number in the tested data sets and image 1150 of FIG. 11B illustrates the distribution of average domain phrases number in the tested data sets.

| Dataset | Stanford test set | UPMC data set | Duke test set | Colorado test set |
| --- | --- | --- | --- | --- |
| Average number of sentences in document | 6.4 | 6.7 | 8.0 | 6.2 |
| Average number of DPs in document | 3.5 | 1.2 | 1.8 | 1.2 |
| Percentage of Document without DPs | 13.7% | 39.6% | 25.7% | 35.9% |

DPs can play an important role in DPA-HNN models in accordance with various embodiments. For example, the Colorado data has an average number of 1.2 DPs in a document, which is much lower than the average number of 3.5 DPs in the Stanford test data. Additionally or alternatively, the percentage of documents without DPs for the Colorado data is much lower than the Stanford test data—which could additionally be a reason why the DPA-HNN model trained on Stanford dataset does not work equally well on Colorado data. However, the average number of sentences in a document for this dataset is 6.2, which is very close to Stanford data of 6.4. Since in HNN model, average sentence number matters, but not DPs, so it explains why HNN model has better performance than DPA-HNN model on Colorado data.

Additionally or alternatively, it can generally be observed that the evaluation scores of the PE Acute/Chronic classification task are lower than the PE Positive/Negative classification task denoting the complexity of the former compared to the later task.

To better understand what information DPA-HNN models in a natural language task are using to make its decisions, methods have been developed to visualize the impact of input words on the output decision.

RNN based models including a DPA-HNN model can predict the classes correctly for the same reports where other models fail to correctly classify a document. Example documents a DPA-HNN model can correctly classify which other network models failed to classify in accordance with many embodiments is illustrated in FIGS. 12A-12B. This is illustrated via a hierarchical attention-based visualization where the where the weight value for each word in the sentence is obtained from the weights learned from word-level attention for the first LSTM layer. The weight value for each sentence in the report is obtained from the weights learned from sentence-level attention for the second LSTM layer. With the weights for both word-level and sentence-level attention, it can be seen that different sentences play different roles in a report and different words play different roles in each sentence toward the final classification of a radiology report. In the negative classification example as illustrated in image 1250 of FIG. 12B, the sentence 3: "there is no filling defect in the central pulmonary artery to indicate a pulmonary embolism" has the highest weight. The word "embolism" has the highest weight in this sentence, and the word "no" has the second highest weight in this sentence. In the positive classification example illustrated in image 1200 of FIG. 12A, the sentence 1: "impression 1 interval decrease in the volume of clot within the pulmonary arterial system" has the highest weight. The word "clot" has the highest weight in this sentence. In various embodiments, RNN based models can capture global context from the data by considering long-term dependency among words.

Figures 13A, 13B:
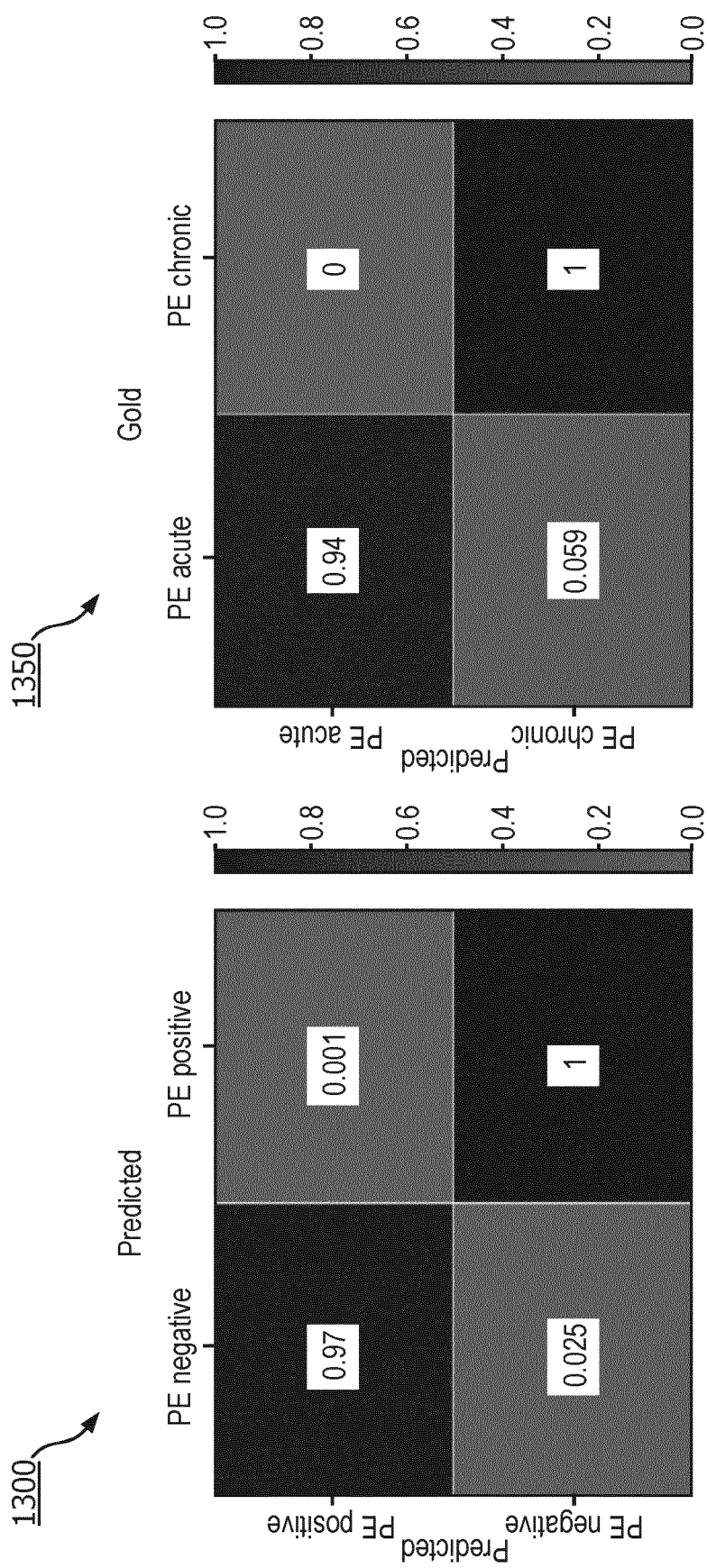
FIG. 13A and FIG. 13B are diagrams illustrating confusion matrices for a HNN-GA model in accordance with various embodiments.

The results in accordance with may embodiments can be further contextualized as a confusion matrix for a DPA-HNN model testing the Stanford test set as illustrated in FIGS. 13A-13B. The confusion matrix is normalized class-wise to meaningfully represent the performance of the model. The X-axis represents gold-standard results, and the Y-axis represents predicted results from a DPA-HNN model in accordance with various embodiments. It can be seen that the false positive (top right part) and the false negative (down left part) rates are very low for both PE Positive/Negative classification as illustrated in image 1300 of FIG. 13A and PE Acute/Chronic classification as illustrated in image 1350 of FIG. 13B. Additionally or alternatively, for both classifications, only two cases are misclassified as illustrated in FIGS. 14A-15B. These errors were evaluated and found to be related to conflicting and skeptical language in the impression. For example, in image 1450 as illustrated in FIG. 14B, the impression clearly states "no definite pulmonary embolus", however, shortly thereafter the report went on to suggest "artifact vs possible pulmonary embolus in the right upper lobe" and recommended an additional imaging test. In the other example as illustrated in image 1550 of FIG. 15B, the model focused on the word "subacute" to predict the report as chronic. Image 1400 as illustrated in FIG. 14A and image 1500 as illustrated in 15A additionally illustrate misclassifications.

Figure 16:
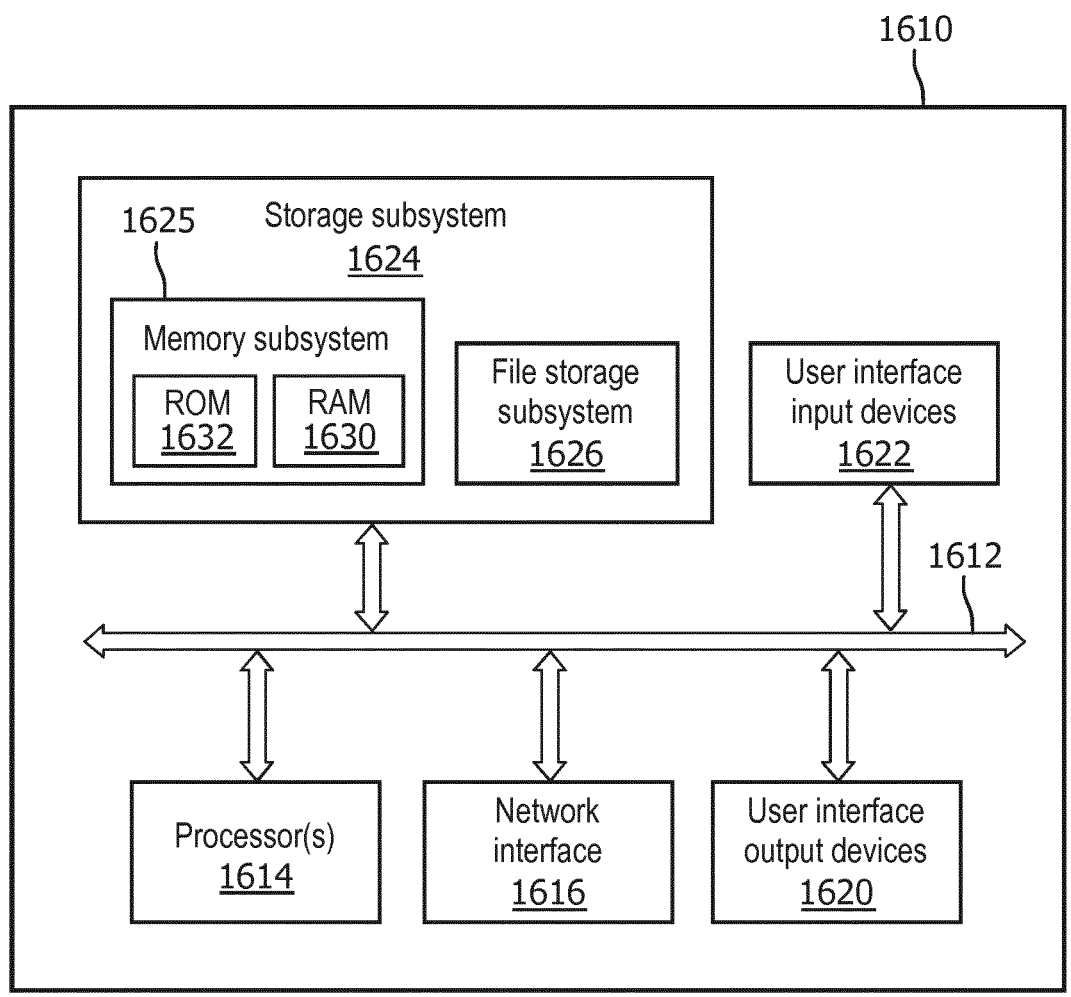
FIG. 16 is a diagram depicting an example computing system architecture.

FIG. 16 is a block diagram of an example computing device 1610 that may optionally be utilized to perform one or more aspects of techniques described herein. In some embodiments, one or more of a client computing device, and/or other component(s) may comprise one or more components of the example computing device 1610.

Computing device 1610 typically includes at least one processor 1614 which communicates with a number of peripheral devices via bus subsystem 1612. These peripheral devices may include a storage subsystem 1624, including, for example, a memory subsystem 1625 and a file storage subsystem 1626, user interface output devices 1620, user interface input devices 1622, and a network interface subsystem 1616. The input and output devices allow user interaction with computing device 1610. Network interface subsystem 1616 provides an interface to outside networks and is coupled to corresponding interface devices in other computing devices.

User interface input devices 1622 may include a keyboard, pointing devices such as a mouse, trackball, touchpad, or graphics tablet, a scanner, a touchscreen incorporated into the display, audio input devices such as voice recognition systems, microphones, and/or other types of input devices. In general, use of the term "input device" is intended to include all possible types of devices and ways to input information into computing device 1610 or onto a communication network.

User interface output devices 1620 may include a display subsystem, a printer, a fax machine, or non-visual displays such as audio output devices. The display subsystem may include a cathode ray tube (CRT), a flat-panel device such as a liquid crystal display (LCD), a projection device, or some other mechanism for creating a visible image. The display subsystem may also provide non-visual display such as via audio output devices. In general, use of the term "output device" is intended to include all possible types of devices and ways to output information from computing device 1610 to the user or to another machine or computing device.

Storage subsystem 1624 stores programming and data constructs that provide the functionality of some or all of the modules described herein. For example, the storage subsystem 1624 may include the logic to perform selected aspects of the processes 100, 150, and/or 200 of FIGS. 1A-1B and 2.

These software modules are generally executed by processor 1614 alone or in combination with other processors. Memory 1625 used in the storage subsystem 1624 can include a number of memories including a main random access memory (RAM) 1630 for storage of instructions and data during program execution and a read only memory (ROM) 1632 in which fixed instructions are stored. A file storage subsystem 1626 can provide persistent storage for program and data files, and may include a hard disk drive, a floppy disk drive along with associated removable media, a CD-ROM drive, an optical drive, or removable media cartridges. The modules implementing the functionality of certain embodiments may be stored by file storage subsystem 1626 in the storage subsystem 1624, or in other machines accessible by the processor(s) 1614.

Bus subsystem 1612 provides a mechanism for letting the various components and subsystems of computing device 1610 communicate with each other as intended. Although bus subsystem 1612 is shown schematically as a single bus, alternative embodiments of the bus subsystem may use multiple busses.

Computing device 1610 can be of varying types including a workstation, server, computing cluster, blade server, server farm, or any other data processing system or computing device. Due to the ever-changing nature of computers and networks, the description of computing device 1610 depicted in FIG. 16 is intended only as a specific example for purposes of illustrating some embodiments. Many other configurations of computing device 1610 are possible having more or fewer components than the computing device depicted in FIG. 16.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A method implemented with one or more processors to generate one or more classifications of a document, comprising:
obtaining data indicative of the document;
processing the data indicative of the document in a first layer of two or more layers of a hierarchical network model using a dual granularity attention mechanism to generate first layer output data, wherein the dual granularity attention mechanism weights some portions of the data indicative of the document in the first layer more heavily, wherein the some portions are integrated into the hierarchical network model during training of the dual granularity attention mechanism, and wherein the dual granularity attention mechanism includes an attention history and a domain-specific attention history, wherein the attention history corresponds with the first layer of the hierarchical network model and the domain-specific attention history corresponds with a second layer of the hierarchical network model;
processing the first layer output data in the second of two or more layers of the hierarchical network model to generate second layer output data, wherein the second layer of the hierarchical network model is specialized to interpret the second layer output data; and
generating a classification label from the second layer output data.

2. The method of claim 1, wherein the two or more layers of the hierarchical network model comprise a word layer and a sentence layer.

3. The method of claim 2, wherein the two or more layers of the hierarchical network model further comprise a character layer, a section layer, and a document layer.

4. The method of claim 3, wherein the character layer further comprises a character Long Short Term Memory ("LSTM") layer wherein a character dual granularity mechanism is applied to the character LSTM layer, the word layer further comprises a word LSTM layer wherein a word dual granularity mechanism is applied to the word LSTM layer, the sentence layer further comprises a sentence LSTM layer wherein a sentence dual granularity mechanism is applied to the sentence LSTM layer, and the section layer further comprises a LSTM layer wherein a section dual granularity layer is applied to the section LSTM layer.

5. The method of claim 1, wherein generating the classification label further comprises feeding the second layer output data into a softmax function.

6. The method of claim 1, wherein the dual granularity attention mechanism is determined by the one or more processors by:

$$e_t = a(h_t, h'_t)$$
$$\alpha_t = \frac{\exp(e_t)}{\sum_{k=1}^{T} epx(e_k)}$$
$$c = \sum_{t=1}^{T} \alpha_t h_t$$

wherein e is an attention value, a is a learnable function, h is the attention history, h' is the domain-specific attention history, α is a probability vector, T is a total number of time steps, t is a time, k is a time, and c is a weighted average.

7. The method of claim 6, wherein the domain-specific attention history is prepopulated with embeddings corresponding to knowledge in a particular domain.

8. At least one non-transitory computer-readable medium storing a machine learning model to generate one or more classifications of a document, wherein the model is trained using the following process:
obtaining a set of training data indicative of the document;
training two or more layers of a hierarchical network model with a dual granularity attention mechanism using the set of training data indicative of the document, wherein a first layer in the dual layer attention mechanism is trained with the two or more layers of the hierarchical network model and a second layer in the dual granularity attention mechanism is prepopulated with data indicative of domain-specific knowledge;
obtaining data indicative of the document;
processing the data indicative of the document in the first layer of two or more layers of a hierarchical network model using the dual granularity attention mechanism to generate first layer output data, wherein the dual granularity attention mechanism weights some portions of the data indicative of the document in the first layer more heavily, and wherein the dual granularity attention mechanism includes an attention history and a domain-specific attention history, wherein the attention history corresponds with the first layer of the hierarchical network model and the domain-specific attention history corresponds with a second layer of the hierarchical network model;
processing the first layer output data in the second of two or more layers of the hierarchical network model to generate second layer output data, wherein the second layer of the hierarchical network model is specialized to interpret the second layer output data; and
generating a classification label from the second layer output data.

9. The at least one non-transitory computer readable medium of claim 8, wherein the two or more layers of the hierarchical network model comprise a word layer and a sentence layer.

10. The at least one non-transitory computer readable medium of claim 9, wherein the two or more layers of the hierarchical network model further comprise a character layer, a section layer, and a document layer.

11. The at least one non-transitory computer readable medium of claim 9, wherein the character layer further comprises a character Long Short Term Memory ("LSTM") layer wherein a character dual granularity mechanism is applied to the character LSTM layer, the word layer further comprises a word LSTM layer wherein a word dual granularity mechanism is applied to the word LSTM layer, the sentence layer further comprises a sentence LSTM layer wherein a sentence dual granularity mechanism is applied to the sentence LSTM layer, and the section layer further comprises a LSTM layer wherein a section dual granularity layer is applied to the section LSTM layer.

12. The at least one non-transitory computer readable medium of claim 8, wherein generating the classification label further comprises feeding the second layer output data into a softmax function.

13. The at least one non-transitory computer readable medium of claim 8, wherein the dual granularity attention mechanism is determined by the one or more processors by:

$$e_t = a(h_t, h'_t)$$

$$\alpha_t = \frac{\exp(e_t)}{\sum_{k=1}^{T} epx(e_k)}$$

$$c = \sum_{t=1}^{T} \alpha_t h_t$$

wherein e is an attention value, a is a learnable function, h is the first layer in the dual layer attention history, h' is the second layer in the dual layer attention history and includes domain-specific knowledge, α is a probability vector, T is a total number of time steps, t is a time, k is a time, and c is a weighted average.

14. The at least one non-transitory computer readable medium of claim 13, wherein the domain-specific attention history is prepopulated with embeddings corresponding to knowledge in a particular domain.

15. A system comprising one or more processors and memory operably coupled with the one or more processors to generate one or more classifications of a document, wherein the memory stores instructions that, in response to execution of the instructions by one or more processors, cause the one or more processors to perform the following operations:

obtaining data indicative of the document;

processing the data indicative of the document in a first layer of two or more layers of a hierarchical network model using a dual granularity attention mechanism to generate first layer output data, wherein the dual granularity attention mechanism weights some portions of the data indicative of the document in the first layer more heavily, wherein the some portions are integrated into the hierarchical network model during training of the dual granularity attention mechanism, and wherein the dual granularity attention mechanism includes an attention history and a domain-specific attention history, wherein the attention history corresponds with the first layer of the hierarchical network model and the domain-specific attention history corresponds with a second layer of the hierarchical network model;

processing the first layer output data in the second of two or more layers of the hierarchical network model to generate second layer output data, wherein the second layer of the hierarchical network model is specialized to interpret the second layer output data; and generating a classification label from the second layer output data.

16. The system of claim 15, wherein the two or more layers of the hierarchical network model comprise a word layer and a sentence layer.

17. The system of claim 16, wherein the two or more layers of the hierarchical network model further comprise a character layer, a section layer, and a document layer.

18. The system of claim 15, wherein generating the classification label further comprises feeding the second layer output data into a softmax function.

* * * * *